United States Patent [19]

Althuis et al.

[11] 4,284,829
[45] Aug. 18, 1981

[54] HYDROXYALKYL AND OXOALKYL SUBSTITUTED PHENOLS AS ANALGESICS AND SEDATIVES

[75] Inventors: Thomas H. Althuis, Groton; Charles A. Harbert, Waterford; Michael R. Johnson; Lawrence S. Melvin, Jr., both of Gales Ferry, all of Conn.

[73] Assignee: Pfizer Inc., New York, N.Y.

[21] Appl. No.: 972,595

[22] Filed: Dec. 22, 1978

Related U.S. Application Data

[62] Division of Ser. No. 832,868, Sep. 13, 1977.

[51] Int. Cl.³ .................... C07C 39/06; C07C 39/10; C07C 47/00
[52] U.S. Cl. .................... 568/764; 568/763; 568/766; 424/256; 424/263; 260/326.47; 544/172; 544/358; 544/360; 544/399; 546/186; 187/546; 546/190; 546/194; 560/163; 560/164; 560/173
[58] Field of Search .................... 568/766, 763, 764; 260/570.5 R, 570.5 C, 570.5 CA, 592, 570 R; 424/256, 263, 273

[56] References Cited

U.S. PATENT DOCUMENTS

| | | | |
|---|---|---|---|
| 3,989,741 | 11/1976 | Parker | 260/590 R |
| 4,026,952 | 5/1977 | Fischer et al. | 568/766 |
| 4,062,978 | 12/1977 | Cole | 260/590 R |

FOREIGN PATENT DOCUMENTS 1479297  7/1977  United Kingdom .................... 568/766

*Primary Examiner*—Werren B. Lone

*Attorney, Agent, or Firm*—Francis X. Murphy; Charles J. Knuth; Albert E. Frost

[57] ABSTRACT

Compounds useful for pharmacological and medicinal purposes having the formulae

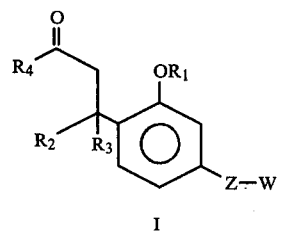

and

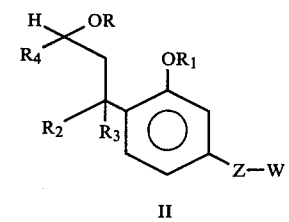

wherein R is H, $C_1$-$C_5$ alkanoyl; $R_1$ is H, benzyl, $C_1$-$C_5$ alkanoyl, $P(O)(OH)_2$, —$CO(CH_2)_2COOH$ or a basic acyl group; each of $R_2$ and $R_4$ is H, $C_1$-$C_6$ alkyl, phenyl, pyridyl or $(CH_2)_yC_6H_5$; y is 1–4; $R_3$ is H or $CH_3$; Z is $C_1$-$C_{13}$ alkylene or —$(alk_1)_m$—O—$(alk_2)_n$—; each of $(alk_1)$ and $(alk_2)$ is $C_1$-$C_{13}$ alkylene with the proviso that the summation of carbon atoms in $(alk_1)$ plus $(alk_2)$ is not greater than 13; each of m and n is 0 or 1; and W is H, pyridyl, phenyl, fluorophenyl or chlorophenyl; intermediates therefor and methods for their preparation and use.

4 Claims, No Drawings

HYDROXYALKYL AND OXOALKYL SUBSTITUTED PHENOLS AS ANALGESICS AND SEDATIVES

CROSS REFERENCE TO RELATED APPLICATION

This application is a division of application Ser. No. 832,868 filed Sept. 13, 1977.

BACKGROUND OF THE INVENTION

Field of the Invention

This invention relates to certain 2-(acyclic substituted) phenols and derivatives thereof having at the 5-position a —Z—W group wherein Z is alkylene having from one to thirteen carbon atoms or (alk$_1$-)$_m$—O—(alk$_2$)$_n$—wherein each of m and n is 0 or 1 and each of (alk$_1$) and (alk$_2$) is alkylene having from one to thirteen carbon atoms with the proviso that the summation of carbon atoms in (alk$_1$) plus (alk$_2$) is not greater than thirteen; and W is hydrogen, phenyl, fluorophenyl, chlorophenyl or pyridyl; derivatives thereof, intermediates therefor and process for their preparation. The products are useful as CNS agents, especially as analgesics, tranquilizers, sedatives and antianxiety agents in mammals, including man, and/or as anticonvulsants, diuretics and antidiarrheal agents in mammals, including man.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side effects. Other potent analgesic agents such as d-propoxyphene, codeine, and morphine, possess addictive liability. The need for improved and potent analgesic agents is, therefore, evident.

More recently, great interest in cannabinol-type compounds as analgesic agents has been exhibited. (R, Mechoulam Ed., "Marijuana. Chemistry, Pharmacology, Metabolism and Clinical Effects", Academic Press, New York, N.Y., 1973; Mechoulam, et al., *Chemical Reviews*, 76, 75–112 [1976]).

SUMMARY OF THE INVENTION

It has now been found that certain 5-substituted phenols having at the 2-position an acyclic ketone or alcohol group are effective as CNS agents, especially as analgesics, tranquilizers, sedatives and antianxiety agents in mammals, including man, and/or as anticonvulsants, diuretics and antidiarrheal agents in mammals, including man (formulae I and II below). Also included in this invention are various derivatives of said compounds which are useful as dosage forms of the compounds, intermediates therefor and methods for their preparation. The compounds and derivatives thereof have the formulae

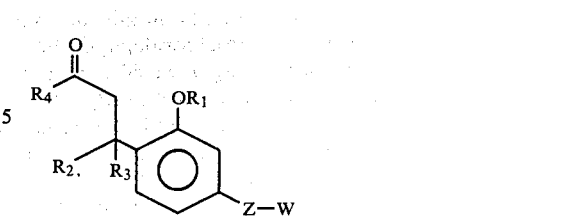

and

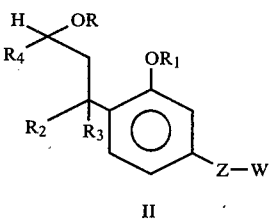

(in which stereochemistry is not represented) wherein:
R is selected from the group consisting of hydrogen and alkanoyl having from one to five carbon atoms;
R$_1$ selected from the group consisting of hydrogen, benzyl, alkanoyl, having from one to five carbon atoms —P(O)(OH)$_2$ and the mono- and disodium and potassium salts thereof, —CO(CH$_2$)$_2$—COOH and the sodium and potassium salts thereof, and —CO—(CH$_2$)$_p$—NR$_5$R$_6$ wherein p is 0 or an integer from 1 to 4; each of R$_5$ and R$_6$ when taken individually is selected from the group consisting of hydrogen and alkyl having from one to four carbon atoms; R$_5$ and R$_6$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;
each of R$_2$ and R$_4$ is selected from the group consisting of hydrogen, alkyl having from one to six carbon atoms, phenyl, pyridyl and phenylalkyl having from one to four carbon atoms in the alkyl moiety;
R$_3$ is selected from the group consisting of hydrogen and methyl;
Z is selected from the group consisting of (a) alkylene having from one to thirteen carbon atoms; (b) —(alk$_1$)$_m$—O—(alk$_2$)$_n$—wherein each of (alk$_1$) and (alk$_2$) is alkylene having from one to thirteen carbon atoms, with the proviso that the summation of carbon atoms in (alk$_1$) plus (alk$_2$) is not greater than thirteen; each of m and n is 0 or 1; and
W is selected from the group consisting of hydrogen, fluoro and chloro.

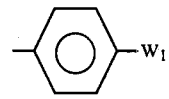

wherein w$_1$ is selected from the group consisting of hydrogen flouro and chloro.

Also included in this invention are the pharmaceutically acceptable acid addition salts of those compounds of formulae I and II which contain a basic group. In compounds having two or more basic groups present, such as those wherein the W variable is pyridyl and/or OR$_1$ represents a basic ester moiety, polyacid addition salts are, of course possible. Representative of such pharmaceutically acceptable acid addition salts are the mineral acid salts such as the hydrochloride, hydrobromide, sulfate, phosphate, nitrate; organic acid salts such as the citrate, acetate, sulfosalicylate, tartrate, glycolate, malate, malonate, maleate, pamoate, salicylate, stearate, phthalate, succinate, gluconate,2-hydroxy-3-naphthoate, lactate, mandelate and methane sulfonate.

Compounds of formula II can exist in diastereomeric forms by virtue of the asymmetric center at which the OR group is attached. Additionally, compounds of fomulae I and II may contain asymmetric centers in the 4-position substituent (Z-W) of the phenyl ring.

For convenience, the above formulae depict the racemic compounds. However, the above formulae are considered to be generic to and embracive of the racemic modifications of the compounds of this invention, the diastereomeric mixtures, the pure enantiomers and diastereomers thereof. The utility of the racemic mixture, the diastereomeric mixture as well as of the pure enantiomers and diastereomers is determined by the biological evaluation procedures described below.

Compounds of formula I wherein $R_1$ is H exist, in solution, in equilibrium with their hemiketal forms. Spectral evidence indicates the hemiketal to be the predominant form. In the solid state, spectral evidence indicates the compounds exist substantially completely in the hemiketal form. The keto and hemiketal forms of compounds of formula I are included in this invention.

Favored because of their greater biological activity relative to that of other compounds described herein, are compounds of formulae I-II wherein R is hydrogen; $R_2$ is hydrogen or alkyl; $R_1$ is hydrogen or alkanoyl; $R_3$ is hydrogen or methyl; and Z and W have the values shown below:

| Z | m | n | W |
|---|---|---|---|
| alkylene having from 5 to 10 carbon atoms | — | — | H |
| alkylene having from 2 to 6 carbon atoms | — | — | 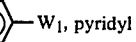—$W_1$, pyridyl |
| $(alk_1)_m$—O—$(alk_2)_n$ | 0 | 1 | 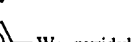—$W_1$, pyridyl |
| $(alk_1)_m$—O—$(alk_2)_n$ | 1 | 0 | 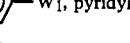—$W_1$, pyridyl |

Preferred compounds of formulae I-II, and especially of formula II, are those preferred compounds wherein Z and W have the values shown:

| Z | W |
|---|---|
| $C(CH_3)_2(CH_2)_6$ | H |
| $CH(CH_3)CH(CH_3)(CH_2)_5$ | H |
| $OCH(CH_3)(CH_2)_3$ | $C_6H_5$ |
| $CH(CH_3)(CH_2)_3$ | $C_6H_5$ | and each of R, $R_1$ and $R_3$ is hydrogen; and each of $R_2$ and $R_4$ is alkyl.

DETAILED DESCRIPTION OF THE INVENTION

Compounds of formula I are prepared by conjugate addition of an appropriate 2-bromo-5-(Z-W substituted) phenol to an $\alpha,\beta$-unsaturated ketone via the Grignard reaction. The process comprises, as first step, protection of the phenolic hydroxy group.

Suitable protecting groups are those which do not interfere with subsequent reactions and which can be removed under conditions which do not cause undesired reactions at other sites of said compounds or of products produced therefrom. Representative of such protective groups are methyl, ethyl, benzyl, or substituted benzyl wherein the substituent is, for example, alkyl having from one to four carbon atoms, halo (Cl, Br, F, I) and alkoxy having from one to four carbon atoms.

The exact chemical structure of the processing group is not critical to this invention since its importance resides in its ability to perform in the manner described above. The selection and identification of appropriate protecting groups can easily and readily be made by one skilled in the art. The suitability and effectiveness of a group as a hydroxy protecting group are determined by employing such a group in the herein-illustrated reaction sequences. It should, therefore, be a group which is easily removed to regenerate the hydroxy group. Methyl is a favored protecting group since it is easily removed by treatment with pyridine hydrochloride. The benzyl group, also a favored protecting group, is removed by catalytic hydrogenolysis or acid hydrolysis.

The protected 2-bromo-5-(Z-W substituted)phenol is then converted to the corresponding Grignard reagent in known manner as, for example, by refluxing a mixture of one molar proportion of the bromo reactant and two molar proportions of magnesium in a reaction-inert solvent, e.g. cyclic and acylic ethers such as tetrahydrofuran, dioxane and dimethyl ether of ethylene glycol. The resulting mixture is then cooled to about 0° C. to −20° C. and a cuprous salt (CuBr, CuCl or CuI) added followed by the appropriate $\alpha,\beta$-unsaturated ketone. A cuprous salt is generally added to increase conjugate addition of the Grignard reagent to the $\alpha,\beta$-unsaturated ketone. The amount of cuprous salt used is not critical but can vary widely. Molar proportions ranging from about 0.2 to about 0.02 moles per mole of bromo reactant afford satisfactory yields of conjugate addition product.

Appropriate $\alpha,\beta$-unsaturated ketones are those of formula III below:

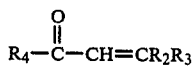
$$R_4-\overset{O}{\underset{\|}{C}}-CH=CR_2R_3 \qquad III$$

wherein $R_2$, $R_3$ and $R_4$ are as defined above.

Many of the $\alpha,\beta$-unsaturated ketones of formula III are known compounds. Those that are not known are conveniently prepared via the reaction of appropriate phosphate carbanions with appropriate aldehydes or ketones according to the Wadsworth-Emmons modifications of the Wittig reaction (J. Am. Chem. Soc., 83, 1733-8, 1961). The reaction, in general, comprises treating a dialkylacylphosphonate with an aldehyde or ketone in an aprotic solvent, e.g. 1,2-dimethoxyethane, diglyme, at a temperature of from about room temperature to about 110° C. Additionally, Grieco et al., J. Am. Chem. Soc., 95, 3071-2 (1973) describe a procedure for preparing dimethyl-(2-oxoalkyl)phosphonates which serve as valuable starting materials in the above-mentioned Wadsworth-Emmons modification of the Wittig reaction. The dialkyl acylphosphonates required for these procedures are prepared by the Michaelis-Arbuzov reaction (Kosolapoff, "Organophosphorous Compounds", 1st Ed., J. Wiley and Sons, Inc., New York, N.Y., 1950, Chapter 7) which comprises reacting a trialkyl phosphite with an appropriate alkyl or aralkyl halide.

A convenient method for preparing compounds of this invention wherein —Z—W is —O—(alk$_2$)$_n$—W comprises the use of 4-bromo resorcinol as starting material. The process comprises protecting the two hydroxy groups of the resorcinol by benzylation according to standard procedures. The benzyl group is favored as protecting group in this method since it can easily be removed by catalytic hydrogenation without cleaving the ether group —O—(alk$_2$)$_n$—W. Other protecting groups groups such as alkyl (e.g., methyl or ethyl) can, of course, also be used. However, the benzyl protecting group is favored since it gives rise to fewer side reactions. The protected 4-bromo resorcinol is then subjected to the Grignard reaction and reacted with the appropriate α,β-unsaturated ketone in a reaction-inert solvent in the manner described above. The (2,4-dibenzyloxyphenyl)alkanone thus produced is then subjected to catalytic hydrogenation over palladium-on-carbon to produce the corresponding (2,4-dihydroxyphenyl)alkanone which exists principally in the form of its hemiketal. The hemiketal is then converted to the corresponding C$_{1-4}$ alkyl, e.g., methyl, ketal by reaction with, for example a trialkyl orthoformte, such as trimethylorthoformate in a suitable solvent such as a C$_{1-4}$ alcohol, e.g., methanol, in the presence of concentrated sulfuric acid. The thus-produced alkyl ketal is then alkylated with the appropriate alkyl or aralkyl methane sulfonate or tosylate in the presence of anhydrous sodium or potassium carbonate in a suitable reaction-inert solvent such as N,N-dimethylformamide at a temperature of from about 75°–100° C. This method has the advantage of permitting the use of simpler compounds throughout the entire sequence of reactions. The O-alkylated oraralkylated/ketal is then deketalized by reaction with, for example, hydrochloric acid, to produce the corresponding (2-hydroxy-4-[O-(alk$_2$)$_n$]phenyl) alkanone which exists principally in the form of its hemiketal.

The 2-bromo-5-(Z-W substituted) phenol reactants are prepared by bromination of the appropriate 3-(Z-W substituted) phenol according to standard procedures as, for example, by treatment with bromine in carbon tetrachloride at a temperature of from about 20°–30° C. The necessary 3-(Z-W substituted) phenols, if not known compounds, are prepared by procedures illustrated herein. A convenient method for preparing such reactants wherein the Z moiety is alkylene or (alk$_1$—O—(alk$_2$)$_n$—comprises the Wittig reaction on an appropriate aldehyde such as 2-(3-hydroxyphenol)-2-methyl propionaldehyde, the hydroxy group of which is protected by benzyl ether formation. The said aldehyde is then treated with the appropriate alkyltriphenylphosphonium bromide, the alkyl group of which extends the propionaldehyde group to the desired length. In a typical procedure, the aldehyde reactant is added to a slurry of dimsyl sodium and alkyl triphenylphosphonium bromide in dimethyl sulfoxide at a temperature below 30° C., e.g. from about 10° to 30° C. When reaction is complete, the alkene substituted protected phenol is recovered by known methods. Hydrogenation of the alkene over palladium-on-carbon then affords the desired 3-(Z-W substituted)phenol. Judicious choice of the starting (3-hydroxyphenyl)-substituted aldehyde and alkyl triphenylphosphonium bromide reactants affords the required 3-(Z-W-substituted)phenol reactants.

A further procedure for making 3-(Z-W substituted) phenols wherein Z is alkylene or (alk$_1$)—O—(alk$_2$)$_n$— comprises the Wittig reaction on an appropriate phenolic aldehyde or ketone, e.g, 3-hydroxybenzaldehyde or a 3-(hydroxyphenyl)alkyl ketone, in which the phenolic hydoxy group is protected as by conversion to the benzyl, methyl or ethyl ether. By choice of appropriate reactants, compounds having straight or branched alkylene groups (Z) can be produced. When a ketone, e.g., 3-hydroxyacetaphenone is used as reactant, compounds wherein Z has a methyl group on the carbon atom adjacent to the phenyl group obtained.

Substitution of a methyl or ethyl group at other sites, e.g., the β-carbon atom of the alkylene group, is achieved by choice of the appropriate carboalkoxy alkylidene triphenylphosphorane, e.g., (C$_6$H$_5$)$_3$P+C(R')—COOC$_2$H$_5$. The unsaturated ester thus produced is reduced to the corresponding alcohol by reacton with lithium aluminum hydride, generally in the presence of a small amount of aluminum chloride. Alternatively, when the phenolic protecting group is other than benzyl (e.g. methyl), the alcohol is produced by catalytic reduction of the unsaturated ester using palladium-carbon, followed by treatment of the saturated ester thus produced with lithium aluminum hydride. Conversion of the alcohol thus produced to the corresponding tosylate or mesylate followed by alkylation of the tosylate or mesylate with an alkali metal salt of the appropriate HO—(alk$_2$)—W reactant, and finally removal of the protecting group affords the desired resorcinol 3-(Z—W substituted) phenol.

A variation of the above sequence comprises bromination of the alcohol rather than converting it to a tosylate or mesylate. Phosphorous tribromide is a convenient brominating agent. The bromo derivative is then reacted with the appropriate HO—(alk$_2$)—W in the presence of a suitable base (Williamson reaction).

The bromo compounds also serve as valuable intermediates for increasing the chain length of the alkylene moiety in the above sequence to give compounds wherein Z is —alkylene—W. The process comprises treating the bromo derivative with triphenyl phosphine to produce the corresponding triphenylphosphonium bromide. Reaction of the triphenylphosphonium bromide with the appropriate aldehyde or ketone in the presence of a base such as sodium hydride or n-butyl lithium affords an unsaturated derivative which is then catalytically hydrogenated to the corresponding saturated compound An alternative method for introducing an alkyl or aralkyl group into the aromatic nucleus, and specifically such a group wherein the carbon atom adjacent the aromatic nucleus is a tertiary carbon atom, comprises acid catalyzed electrophilic substitution of guaiacol with a tertiary alcohol in the presence of an acid. e.g. methane sulfonic acid. The general procedure consists in reacting a mixture of methanesulfonic acid and equimolar amounts of guaiacol and tertiary alcohol at temperatures of from about 30° C. to about 80° C. until reaction is substantially complete. The product is isolated by pouring the reaction mixture onto ice followed by extraction with a suitable solvent such as methylene chloride. The 2-methoxy-4-alkyl phenol is then converted to the desired 3-alkyl phenol by removal of the phenolic hydroxy group. The process comprises converting the hydroxy group to a dialkyl phosphate group by reaction with a dialkyl chlorophosphonate, e.g. diethyl chlorophosphonate, or with diethyl phosphonate and triethylamine. Treatment of the dialkyl phosphate with lithium/ammonia followed by demethylation of the resulting alkylated methyl ether with boron tribromide or pyridine hydrochloride or other known demethylating agents affords the desired 3-alkylphenol.

Esters of compounds of formulae I and II wherein $R_1$ is alkanoyl or $-CO-(CH_2)_pNR_4R_5$ are readily prepared by reacting formulae I and II compounds wherein $R_1$ is hydrogen with the appropriate alkanoic acid or acid of formula $HOOC-(CH_2)_p-NR_4R_5$ in the presence of a condensing agent such as dicyclohexylcarbodiimide. Alternatively, they are prepared by reaction of a formula I or II compound with the appropriate alkanoic acid chloride or anhydride, e.g., acetyl chloride or acetic anhydride, in the presence of a base such as pyridine.

Phosphate esters are prepared by treating the appropriate compound of formula I or II with potassium hydride followed by dibenzylphosphorochloridate. Catalytic hydrogenation of the dibenzylphosphate ester affords the desired phosphate ester. Cautious neutralization with sodium or potassium hydroxide provides the corresponding sodium or potassium salts.

The analgesic properties of the compounds of this invention are determined by tests using nociceptive stimuli.

Tests Using Thermal Nociceptive Stimuli (a) Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛-inch thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½-inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}=4-5.6$ mg./kg. (s.c.).

(b) Mouse Tail Flick Analgesic Testing

Tail flick testing in mice is modified after D'Amour and Smith, *J. Pharmacol. Exp. Ther.*, 72, 74–79 (1941) using controlled high intensity heat applied to the tail. Each mouse is placed in a snug-fitting metal cylinder, with the tail protruding through one end. This cylinder is arranged so that the tail lies flat over a concealed heat lamp. At the onset of testing an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptable procedure developed by Benbasset, et al., *Arch. int. Pharmacodyn.*, 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

Tests Using Pressure Nociceptive Stimuli

Effect on the Haffner Tail Pinch Procedure

A modification of the procedure of Haffner, *Experimentelle Prufung Schmerzstillender. Mittel Deutch Med. Wschr.*, 55, 731–732 (1929) is used to ascertain the effects of the test compound on aggressive attacking responses elicited by a stimulus pinching the tail. Male albine rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg. (i.p.)

Tests Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\%MPE = \frac{\text{test time} - \text{control time}}{\text{cutoff time} - \text{control time}} \times 100$$

The compounds of the present invention are active analgesics via oral and parenteral administration and are conveniently administered in composition form. Such compositions include a pharmaceutical carrier selected on the basis of the chosen route of administrtion and standard pharmaceutical practice. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 0.20 to about 250 mg. are suitable for most applications.

The physician will determine the dosage which will be most suitable for an individual patient and it will vary with the age, weight and response of the particular patient and the route of administrtion. Generally, however, the initial analgesic dosage in adults may range from about 1.0 to about 1500 mg. per day in single or divided doses. In many instances, it is not necessary to exceed 250 mg. daily. The favored oral dosage range is from about 1.0 to about 300 mg./day; the preferred range is from about 1.0 to about 100 mg./day. The favored parenteral dose is from about 1.0 to about 100 mg./day; the preferred range from about 1.0 to about 50 mg./day.

This invention also provides pharmaceutical compositions, including unit dosage forms, valuable for the use of the herein described compounds as analgesics and other utilities disclosed herein. The dosage form can be given in single or multiple doses, as previously noted, to achieve the daily dosage effective for a particular utility.

The compounds (drugs) described herein can be formulated for administration in solid or liquid form for oral or parenteral administration. Capsules containing drugs of this invention are prepared by mixing one part by weight of drug with nine parts of excipient such as starch or milk sugar and then loading the mixture into telescoping gelatin capsules such that each capsule contains 100 parts of the mixture. Tablets containing said compounds are prepared by compounding suitable mixtures of drug and standard ingredients used in preparing tablets, such as starch, binders and lubricants, such that each tablet contains from 0.20 to 250 mg. of drug per tablet.

Suspensions and solutions of these drugs are frequently prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

Their activity as diuretic agents is determined by the procedure of Lipschitz et al., *J. Pharmacol.*, 197, 97 (1943) which utilizes rats as the test animals. The dosage range for this use is the same as that noted above with respect to the use of the herein described compounds as analgesic agents.

Antidiarrheal utility is determined by a modification of the procedure of Neimegeers et al., *Modern Pharmacology-Toxicology*, Willem van Bever and Harbans Lal, Eds., 7, 68–73 (1976). Charles River CD-1 rats (170–200 gms) are housed in group cages 18 hours before testing. The animals are fasted overnight with water available ad libitum prior to administration of castor oil. The test drug is administered subcutaneously or orally at a constant volume of 5 ml./kg. of body weight in a 5% ethanol, 5% Emulphor EL-620 (a polyoxyethylated vegetable oil emulsifying agent available from Antara Chemicals, New York, N.Y.), and 90% saline vehicle followed one hour later with a challenge of castor oil (one ml., orally). The animals are placed in small individual cages (20.5×16×21 cm.) having suspended wire floors. A disposable cardboard sheet is placed beneath the wire floors and examined one hour after castor oil challenge for the presence or absence of diarrhea. A vehicle/castor oil treatment group serves as control for each day's testing. Results are recorded as the number of animals protected at one hour post challenge. In general, the dosage levels for use of these compounds as antidiarrheal agents parallels those with respect to their use as analgesic agents.

The tranquilizer activity of the compounds of this invention is determined by orally administering them to rats at doses of from about 0.01 to about 50 mg./kg. of body weight and observing the subsequent decreases in spontaneous motor activity. The daily dosage range in mammals is from about 0.01 to about 100 mg.

Anticonvulsant activity is determined by subcutaneously administering the test compound to male Swiss mice (Charles River) weighing 14–23 g. in a vehicle of the type used for antidiarrheal utility. The mice are used in groups of five. The day before use, the mice are fasted overnight but watered ad lib. Treatments are given at volumes of 10 ml. per kg. via a 25 gauge hypodermic needle. Subjects are treated with the test compound and, one hour after challenge, electroconvulsive shock, 50 mA. at 60 Hz. administered transcorneally. Controls are simultaneously run in which the mice are given only the vehicle as control treatment. The electroconvulsive shock treatment produces tonic extensor convulsions in all control mice with a latency of 1.5–3 seconds. Protection is recorded when a mouse exhibits no tonic extensor convulsions for 10 seconds after administration of electroconvulsive shock.

Antianxiety activity is determined in a manner similar to that for evaulating anticonvulsant activity except that the challenge convulsant is pentylenetetrazole, 120 mg./kg. administered intraperitoneally. This treatment produces clonic convulsions in less than one minute in over 95% of control mice treated. Protection is recorded when the latency to convulse is delayed at least 2-fold by a drug pretreatment.

Sedative/depressant activity is determined by treating groups of six mice subcutaneously with various doses of test agents. At 30 and 60 minutes post treatment, the mice are placed on a rotorod for one minute and evaluated for their performance on the rotorod. Inability of the mice to ride the rotorod is taken as evidence of sedative/depressant activity.

EXAMPLE 1

4-[2-Benzyloxy-4-(1,1-dimethylheptyl)phenyl]-2-butanone

A solution of 3.89 g. (0.010 mol.) of 1-bromo-2-benzyloxy-4-(1,1-dimethylheptyl)benzene in 15 ml. of tetrahydrofuran is slowly added to 0.36 g. (0.015 mol.) of 70–80 mesh magnesium metal. The resultant mixture is refluxed for 20 minutes and is then cooled to $-10°$ C. Cuprous iodide (0.115 g., 0.006 mol.) is added and stirring continued for 10 minutes. To the resultant mixture is slowly added a solution of 0.701 g. (0.010 mol.) of methyl vinyl ketone in 5 ml. of tetrahydrofuran at such a rate that the reaction temperature could be maintained below 0° C. The reaction mixture is stirred for 30 minutes longer (t<0° C.) and is then added to 100 ml. of 1N hydrochloric acid and 100 g. of ice. The quenched reaction is extracted three times with 150 ml. portions of ether. The combined ether extract is washed twice with 100 ml. portions of water, twice with 100 ml. portions of saturated sodium chloride, dried over magnesium sulfate and evaporated to an oil. The oil was purified via column chromatography on 180 g. of silica gel eluted with 20% ether-cyclohexane to yield 1.07 g. (28%) of the title compound as an oil.

PMR $\delta_{CDCl_3}{}^{TMS}$ 0.80 (m, terminal sidechain methyl), 1.22 (s, gem dimethyl), 2.03 (s, CH$_3$CO), 2.72 (m, two methylenes), 5.00 (s, benzyl ether methylene), 6.6–6.8 (m, ArH), 6.90 (d, J=8 Hz, ArH) and 7.22 (bs, PhH).

The above procedure is repeated but using the appropriate alkenone as reactant in place of methyl vinyl ketone and the appropriate 1-bromo-2-benzyloxy-4-(Z-W)benzene to prepare:

4-[2-benzyloxy-4-(1,1-dimethylheptyl)phenyl]-2-pentanone as an oil (3.99 g., 66%) from 1.26 g. (0.0154 mol.) of 3-penten-2-one and 6.0 g. (0.0154 mol.) of 1-bromo-2-benzyloxy-4-(1,1-dimethylheptyl)benzene.

PMR $\delta_{CDCl_3}{}^{TMS}$ 0.81 (m, terminal sidechain methyl), 1.24 (s, gem dimethyl), 2.00 (s, CH$_3$CO), 2.65 (m, OCCH$_2$), 3.2–4.0 (m, benzylic methine), 5.07 (s, benzyl ether methylene), 6.85 (m, ArH), 7.07 (d, J=8 Hz, ArH) and 7.34 (bs, PhH).

IR: (CHCl$_3$) 1715, 1613 and 1575 cm$^{-1}$.

MS: m/e 394 (M+), 337, 323 and 309.

EXAMPLE 2

4-[4-(1,1-Dimethylheptyl)-2-hydroxyphenyl]-2-butanone

A mixture of 0.5 g. (1.31 mmols.) of 4-[2-benzyloxy-4-(1,1-dimethylheptyl)phenyl]-2-butanone, 360 mg. of solid sodium bicarbonate, 100 mg. of 10% palladium-on-carbon and 10 ml. of ethanol is stirred under one atmosphere of hydrogen pressure for one hour. The reaction mixture is filtered through diamtomaceous earth with ethyl acetate and the filtrate evaporated to an oil. The oil is purified via column chromatography on 100 g. of silica gel eluted with 50% ether-cyclohexane to yield 247 mg. (93%) of the title compound as an oil.

PMR: $\delta_{CDCl_3}{}^{TMS}$ 0.82 (m, terminal sidechain methyl), 1.22 (s, gem dimethyl), 1.60 and 2.15 (s, ratio 1:3, hemiketal and ketone forms), 2.80 (bs, two methylenes) and 6.7–7.3 (m, ArH).

IR: (CHCl$_3$) 3636, 3571, 3289, 1706, 1623, 1603 and 1572 cm$^{-1}$.

MS: m/e 290 (M+), 275, 272, 257, 205 and 187.

By means of the above procedure, the following compound is prepared from the appropriate compound of Example 1.

4-[4-(1,1-dimethylheptyl)-2-hydroxyphenyl]-2-pentanone (0.49 g., 35%) from 1.8 g. (4.60 mmols.) of 4-[2-benzyloxy-4-1,1-dimethylheptyl)phenyl]-2-pentanone; M.P. 79.5°–80.5° C. (from pentane).

PMR: $\delta_{CDCl_3}{}^{TMS}$ 0.84 (m, terminal sidechain methyl), 1.27 (s, gem dimethyl), 1.64 and 2.07 (s, hemiketal and methyl ketone methyls), 6.75–7.25 (m, ArH).

IR: (CHCl$_3$) 3571, 3333, 1706 (w), 1623 and 1572 cm$^{-1}$.

MS: m/e 304 (M+), 289, 271, 247 and 219 cm$^{-1}$.

Analysis: Anal. Calc'd. for C$_{20}$H$_{32}$O$_2$: C, 78.89; H, 10.59%. Found: C, 79.06; H, 10.56%.

EXAMPLE 3

4-[2-Benzyloxy-4-(1,1-dimethylheptyl)phenyl]-2-butanol

To a $-15°$ C. solution of 0.5 g. (1.31 mmols.) of 4-[2-benzyloxy-4-(1,1-dimethylheptyl)phenyl]-2-butanone (the produce of Example 1) in 5 ml. of methanol is added 50 mg. (1.31 mmols.) of sodium borohydride. The reaction mixture is stirred for 30 minutes and is then added to 100 ml. of saturated sodium chloride-150 ml. ether. The ether extract is washed once with 100 ml. of saturated sodium chloride, dried over magnesium sulfate and evaporated to an oil. The oil is purified via column chromatography on 100 g. of silica gel eluted with 1:1 ether:cyclohexane to yield 419 mg. (84%) of the title compound as an oil.

PMR: $\delta_{CDCl_3}{}^{TMS}$ 0.8 (m, terminal sidechain methyl), 1.10 (d, J=7 Hz, carbinol methyl), 1.23 (s, gem dimethyl), 2.6–2.9 (m, two methylenes), 3.63 (sextet, carbinol methine), 5.00 (s, benzyl ether methylene), 6.8–7.3 (m, ArH) and 7.30 (bs, PhH).

In like manner, the 2-pentanone compound of Example 1 is reduced to give:

4-[2-benzyloxy-4-(1,1-dimethylheptyl)phenyl]-2-pentanol (273 mg., 15%) of diastereomer A and 825 mg. (45%) of diastereomer B, both as oils, from 1.8 g. (4.60 mmols.) of 4-[2-benzyloxy-4-(1,1-dimethylheptyl)-phenyl]-2-pentanone.

Diastereomer A:

PMR: $\delta_{CDCl_3}{}^{TMS}$ 0.85 (m, terminal sidechain methyl), 1.08 (d, J=6 Hz, methyl), 1.29 (s, gem dimethyl), 3.5 (m, carbinol and benzylic methines), 5.09 (s, benzyl ether methylene), 7.0 (m, ArH) and 7.40 (bs, PhH).

IR: (CHCl$_3$) 3497, 1613 and 1572 cm$^{-1}$.

MS: m/e 396 (M+), 381, 311 and 91.

Diastereomer B:

PMR: $\delta_{CDCl_3}{}^{TMS}$ 0.85 (m, terminal sidechain methyl), 1.28 (s, gem dimethy), 3.40 (m, methine), 3.80 (m, methine), 5.10 (s, benzyl ether methylene), 6.90 (m, ArH), 7.17 (d, J=8 Hz, ArH) and 7.42 (bs, PhH).

IR: (CHCl$_3$) 3546, 1616 and 1575 cm$^{-1}$.

MS: m/e 396 (M+), 381,311 and 91.

EXAMPLE 4

4-[4-(1,1-Dimethylheptyl)-2-hydroxyphenyl]-2-butanol

A mixture of 390 mg. (1.02 mmols.) of 4-[2-benzyloxy-4-(1,1-dimethylheptyl)phenyl]-2-butanol, 360 mg. of solid sodium bicarbonate, 100 mg. of 10% palladium-on-carbon and 10 ml. of ethanol is stirred under one atmosphere of hydrogen for 20 minutes. The reaction mixture is filtered through diatomaceous earth with ethyl acetate and evaporated to an oil. The oil is purified via rapid column chromatography on silica gel eluted with ether to give a quantitative yield of the title compound as an oil.

PMR: $\delta_{CDCl_3}{}^{TMS}$ 0.85 (m, terminal sidechain methyl), 1.25 (s, gem dimethyl), 1.62 (m, C-3 methylene), 2.6 (m, C-4 methylene), 3.9 (m, C-2 methine and two OH), 6.90 (dd, J=8 and 2 Hz, ArH), 6.86 (d, J=2 Hz, ArH) and 7.02 (d, J=8 Hz, ArH).

IR: (CHCl$_3$) 3597, 3300, 1629 and 1575 cm$^{-1}$.

MS: m/e 292 (M+), 274, 233, 207 and 189.

Similarly, the following compounds are prepared from corresponding benzyl ethers:

4-[4-(1,1-dimethylheptyl)-2-hydroxyphenyl]-2-pentanol diastereomer A, (179 mg., 98%) from diastereomer A of 4-[2-benzyloxy-4-(1,1-dimethylheptyl)phenyl]-2-pentanol (236 mg., 0.595 mmol.) as an oil.

PMR: $\delta_{CDCl_3}{}^{TMS}$ 0.85 (m, terminal sidechain methyl), 1.28 (s, gem dimethyl), 3.50 (m, carbinol and benzylic methine), 6.82 (d, J=2 Hz, ArH), 6.84 (dd, J=8 and 2 Hz, ArH) and 7.16 (d, J=8 Hz, ArH).

IR: (CHCl$_3$) 3610, 3333, 1634 and 1577 cm$^{-1}$,

MS: m/e 306 (M+), 291, 288, 273, 221 and 203.

Anal. Calc'd. for $C_{20}H_{34}O_2$: C, 78.38; H, 11.18%. Found: C, 78.26; H, 11.07%. 4-[4-(1,1-dimethylheptyl)-2-hydroxyphenyl]-2-pentanol diastereomer B (quantitative yield) from 804 mg. (2.03 mmols.) of 4-[2-benzyloxy-4-(1,1-dimethylheptyl)phenyl]-2-pentanol diastereomer B, as an oil.

PMR: $\delta_{CDCl_3}{}^{TMS}$ 0.85 (m, terminal sidechain methyl), 3.19 (sextet, J=6 Hz, benzylic methine), 3.99 (sextet, J=6 Hz, carbinol methine), 6.82 (d, J=2 Hz, ArH), 6.88 (dd, J=8 and 2 Hz, ArH) and 7.13 (d, J=8 Hz, ArH).

IR: (CHCl$_3$) 3610, 3378, 1629 and 1575 cm$^{-1}$.

MS: m/e 306 (M+), 291, 288, 221 and 203.

EXAMPLE 5

The compounds tabulated below are prepared from appropriate 2-bromo-5-(Z-W substituted)phenol benzyl ethers and α,β-unsaturated reactants R$_4$—CO—CH=CR$_2$R$_3$ according to the procedures of Examples 1-2. They exist principally in the hemiketal form.

| R$_4$ | R$_2$ | R$_3$ | Z | W |
|---|---|---|---|---|
| n-C$_3$H$_7$ | H | H | C(CH$_3$)$_2$(CH$_2$)$_6$ | H |
| i-C$_3$H$_7$ | H | H | C(CH$_3$)$_2$(CH$_2$)$_6$ | H |
| t-C$_4$H$_9$ | H | H | C(CH$_3$)$_2$(CH$_2$)$_6$ | H |
| n-C$_6$H$_{13}$ | H | H | C(CH$_3$)$_2$(CH$_2$)$_6$ | H |
| C$_6$H$_5$ | H | H | C(CH$_3$)$_2$(CH$_2$)$_6$ | H |
| (CH$_2$)C$_6$H$_5$ | H | H | C(CH$_3$)$_2$(CH$_2$)$_6$ | H |
| (CH$_2$)$_4$C$_6$H$_5$ | H | H | C(CH$_3$)$_2$(CH$_2$)$_6$ | H |
| C$_2$H$_5$ | CH$_3$ | H | C(CH$_3$)$_2$(CH$_2$)$_6$ | H |
| n-C$_4$H$_9$ | CH$_3$ | H | C(CH$_3$)$_2$(CH$_2$)$_6$ | H |
| C$_6$H$_5$ | CH$_3$ | H | C(CH$_3$)$_2$(CH$_2$)$_6$ | H |
| (CH$_2$)$_3$C$_6$H$_5$ | CH$_3$ | H | C(CH$_3$)$_2$(CH$_2$)$_6$ | H |
| CH$_3$ | C$_2$H$_5$ | H | C(CH$_3$)$_2$(CH$_2$)$_6$ | H |
| CH$_3$ | n-C$_3$H$_7$ | H | C(CH$_3$)$_2$(CH$_2$)$_6$ | H |
| CH$_3$ | n-C$_6$H$_{13}$ | H | C(CH$_3$)$_2$(CH$_2$)$_6$ | H |
| CH$_3$ | C$_6$H$_5$ | H | C(CH$_3$)$_2$(CH$_2$)$_6$ | H |
| CH$_3$ | C$_6$H$_5$ | CH$_3$ | C(CH$_3$)$_2$(CH$_2$)$_6$ | H |
| C$_2$H$_5$ | n-C$_3$H$_7$ | H | C(CH$_3$)$_2$(CH$_2$)$_6$ | H |
| CH$_3$ | i-C$_3$H$_7$ | H | C(CH$_3$)$_2$(CH$_2$)$_6$ | H |
| C$_2$H$_5$ | i-C$_3$H$_7$ | H | C(CH$_3$)$_2$(CH$_2$)$_6$ | H |
| CH$_2$C$_6$H$_5$ | n-C$_4$H$_9$ | H | C(CH$_3$)$_2$(CH$_2$)$_6$ | H |
| CH$_2$C$_6$H$_5$ | C$_2$H$_5$ | CH$_3$ | C(CH$_3$)$_2$(CH$_2$)$_6$ | H |
| CH$_2$C$_6$H$_5$ | CH$_2$C$_6$H$_5$ | H | C(CH$_3$)$_2$(CH$_2$)$_6$ | H |
| CH$_2$C$_6$H$_5$ | C$_6$H$_5$ | H | C(CH$_3$)$_2$(CH$_2$)$_6$ | H |
| (CH$_2$)$_4$C$_6$H$_5$ | CH$_3$ | H | C(CH$_3$)$_2$(CH$_2$)$_6$ | H |
| (CH$_2$)$_4$C$_6$H$_5$ | n-C$_6$H$_{13}$ | H | C(CH$_3$)$_2$(CH$_2$)$_6$ | H |
| (CH$_2$)$_3$C$_6$H$_5$ | n-C$_4$H$_9$ | CH$_3$ | C(CH$_3$)$_2$(CH$_2$)$_6$ | H |
| CH$_3$ | H | CH$_3$ | CH(CH$_3$)CH(CH$_3$)(CH$_2$)$_5$ | H |
| CH$_3$ | CH$_3$ | CH$_3$ | (CH$_2$)$_5$ | H |
| n-C$_3$H$_7$ | H | CH$_3$ | C(CH$_3$)$_2$(CH$_2$)$_8$ | H |
| CH$_3$ | H | CH$_3$ | (CH$_2$)$_{13}$ | H |
| n-C$_6$H$_{13}$ | H | CH$_3$ | (CH$_2$)$_{13}$ | H |
| i-C$_3$H$_7$ | H | CH$_3$ | (CH$_2$)$_9$ | H |
| C$_6$H$_5$ | CH$_3$ | CH$_3$ | (CH$_2$)$_{11}$ | H |

-continued

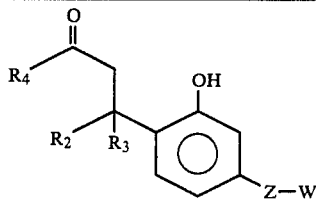

| R4 | R2 | R3 | Z | W |
|---|---|---|---|---|
| (CH$_2$)$_3$C$_6$H$_5$ | H | CH$_3$ | C(CH$_3$)$_2$(CH$_2$)$_{10}$ | H |
| CH$_3$ | H | CH$_3$ | CH(CH$_3$)(CH$_2$)$_3$ | C$_6$H$_5$ |
| CH$_3$ | CH$_3$ | CH$_3$ | CH(CH$_3$)(CH$_2$)$_3$ | 4-FC$_6$H$_4$ |
| sec-C$_4$H$_9$ | C$_2$H$_5$ | H | CH(CH$_3$)(CH$_2$)$_4$ | 4-ClC$_6$H$_4$ |
| C$_2$H$_5$ | n-C$_5$H$_{11}$ | H | (CH$_2$)$_9$ | C$_6$H$_5$ |
| C$_6$H$_5$ | CH$_3$ | H | CH(C$_2$H$_5$)(CH$_2$)$_2$ | 4-ClC$_6$H$_4$ |
| CH$_3$ | (CH$_2$)$_3$C$_6$H$_5$ | H | C(CH$_3$)$_2$(CH$_2$)$_{10}$ | C$_6$H$_5$ |
| CH$_3$ | H | CH$_3$ | O(CH$_2$)$_4$ | C$_6$H$_5$ |
| i-C$_6$H$_{13}$ | H | CH$_3$ | OCH(CH$_3$)(CH$_2$)$_3$ | C$_6$H$_5$ |
| C$_6$H$_5$ | CH$_3$ | CH$_3$ | OCH(CH$_3$)(CH$_2$)$_3$ | C$_6$H$_5$ |
| (CH$_2$)$_2$C$_6$H$_5$ | C$_2$H$_5$ | H | O(CH$_2$)$_3$ | 4-ClC$_6$H$_4$ |
| CH$_3$ | C$_6$H$_5$ | H | O(CH$_2$)$_4$ | C$_6$H$_5$ |
| n-C$_6$H$_{13}$ | (CH$_2$)$_4$C$_6$H$_5$ | H | O(CH$_2$)$_4$ | C$_6$H$_5$ |
| C$_6$H$_5$ | C$_6$H$_5$ | H | O(CH$_2$)$_{10}$ | 4-ClC$_6$H$_4$ |
| CH$_2$C$_6$H$_5$ | C$_6$H$_5$ | CH$_3$ | OCH(CH$_3$)(CH$_2$)$_8$ | C$_6$H$_5$ |
| CH$_3$ | (CH$_2$)$_4$C$_6$H$_5$ | H | OCH(CH$_3$)(CH$_2$)$_{10}$ | 4-FC$_6$H$_4$ |
| C$_6$H$_5$ | C$_6$H$_5$ | H | O(CH$_2$)$_{13}$ | C$_6$H$_5$ |
| (CH$_2$)$_2$C$_6$H$_5$ | i-C$_6$H$_{13}$ | H | O(CH$_2$)$_4$ | C$_6$H$_5$ |
| CH$_3$ | CH$_3$ | H | (CH$_2$)$_3$O(CH$_2$)$_3$ | H |
| n-C$_6$H$_{13}$ | CH$_3$ | H | (CH$_2$)$_4$OCH$_2$ | H |
| CH$_3$ | CH$_3$ | H | (CH$_2$)$_{13}$O | H |
| n-C$_3$H$_7$ | i-C$_3$H$_7$ | H | C(CH$_3$)$_2$(CH$_2$)$_2$O(CH$_2$)$_4$ | H |
| C$_6$H$_5$ | H | CH$_3$ | (CH$_2$)$_4$O | C$_6$H$_5$ |
| CH$_3$ | C$_6$H$_5$ | H | (CH$_2$)$_6$O(CH$_2$)$_7$ | H |
| CH$_2$C$_6$H$_5$ | (CH$_2$)$_4$C$_6$H$_5$ | H | CH(CH$_3$)(CH$_2$)$_2$O | C$_6$H$_5$ |
| n-C$_6$H$_{13}$ | H | H | C(CH$_3$)$_2$(CH$_2$)$_6$ | H |
| C$_6$H$_5$ | H | H | C(CH$_3$)$_2$(CH$_2$)$_7$ | H |
| CH$_2$C$_6$H$_5$ | H | H | CH(CH$_3$)CH(CH$_3$)(CH$_2$)$_5$ | H |
| (CH$_2$)$_3$C$_6$H$_5$ | H | H | C(CH$_3$)$_2$(CH$_2$)$_6$ | H |
| CH$_3$ | H | H | OCH(CH$_3$)(CH$_2$)$_3$ | C$_6$H$_5$ |
| t-C$_4$H$_9$ | H | H | O(CH$_2$)$_4$ | C$_6$H$_5$ |
| C$_6$H$_5$ | H | H | (CH$_2$)$_6$O | 4-FC$_6$H$_4$ |
| CH$_2$C$_6$H$_5$ | H | H | (CH$_2$)$_{13}$O | 4-FC$_6$H$_4$ |
| (CH$_2$)$_4$C$_6$H$_5$ | H | H | (CH$_2$)$_6$O(CH$_2$)$_7$ | C$_6$H$_5$ |
| i-C$_4$H$_9$ | H | H | CH O(CH$_2$)$_2$CH(CH$_3$)$_2$ | C$_6$H$_5$ |
| 2-pyridyl | H | H | C(CH$_3$)$_2$(CH$_2$)$_6$ | H |
| 3-pyridyl | H | H | C(CH$_3$)$_2$(CH$_2$)$_6$ | H |
| 4-pyridyl | H | H | C(CH$_3$)$_2$(CH$_2$)$_6$ | H |
| 4-pyridyl | H | CH$_3$ | C(CH$_3$)$_2$(CH$_2$)$_6$ | H |
| 2-pyridyl | CH$_3$ | CH$_3$ | C(CH$_3$)$_2$(CH$_2$)$_6$ | H |
| 4-pyridyl | n-C$_3$H$_7$ | H | C(CH$_3$)$_2$(CH$_2$)$_6$ | H |
| 2-pyridyl | i-C$_6$H$_{13}$ | CH$_3$ | C(CH$_3$)$_2$(CH$_2$)$_6$ | H |
| 4-pyridyl | C$_6$H$_5$ | CH$_3$ | C(CH$_3$)$_2$(CH$_2$)$_6$ | H |
| 3-pyridyl | C$_6$H$_5$ | H | C(CH$_3$)$_2$(CH$_2$)$_6$ | H |
| 2-pyridyl | CH$_2$C$_6$H$_5$ | CH$_3$ | C(CH$_3$)$_2$(CH$_2$)$_6$ | H |
| 4-pyridyl | (CH$_2$)$_3$C$_6$H$_5$ | H | C(CH$_3$)$_2$(CH$_2$)$_6$ | H |
| 4-pyridyl | 4-pyridyl | H | O(CH$_2$)$_4$ | C$_6$H$_5$ |
| 2-pyridyl | 2-pyridyl | H | OCH(CH$_3$)(CH$_2$)$_3$ | C$_6$H$_5$ |

EXAMPLE 6

The compounds of Example 5 are reduced and debenzylated according to the procedures of Examples 3 and 4 to produce diastereomeric compounds having the formula wherein R$_2$, R$_3$, R$_4$, Z and W are as defined in Example 5:

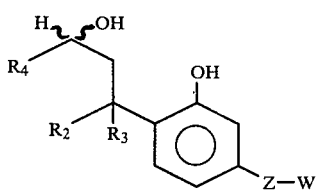

EXAMPLE 7

4-[2-Acetoxy-4-(1,1-dimethylheptyl)phenyl]-2-butanone

A solution of 2.0 g. of 4-[2-hydroxy-4-(1,1-dimethylheptyl)phenyl]-2-butanone in 15 ml. of pyridine is treated at 10° C. with 10 ml. acetic anhydride and the mixture stirred for 18 hours under nitrogen. It is then poured onto ice/water and acidified with dilute hydrochloric acid. The acidified mixture is extracted with ethyl acetate (2×100 ml.), the extracts combined, washed with brine and dried (MgSO$_4$). Evaporation under reduced pressure affords the title product as an oil.

Similarly, the remaining compounds of this invention of formulae I–II are converted to their monoacetoxy esters (of the phenolic hydroxy group) and by substitution of anhydrides of propionic, butyric and valeric acid for acetic anhydride, to the corresponding ester derivatives.

EXAMPLE 8

2-Acetoxy-4-[2-acetoxy-4-(1,1-dimethylheptyl)phenyl]-pentane Diastereomer A

To a solution of 2.0 g. of 4-[2-hydroxy-4-(1,1-dimethylheptyl)phenyl]-2-pentanol diastereomer A in 20 ml. of pyridine at 10° C. is added 20 ml. of acetic anhydride and the mixture stirred under nitrogen for 18 hours. It is then poured onto ice/water and acidified with dilute hydrochloric acid. The product is isolated by extraction with ethyl acetate (2×100 ml.). The combined extracts are washed with brine, dried (MgSO$_4$) and evaporated to give the diacetyl derivatives as an oil.

In like manner, the compounds of formula I wherein R is hydrogen and R$_1$ is hydrogen are converted to their diacyl derivatives. Replacement of acetic anhydride by propionic, butyric or valeric acid anhydrides affords the corresponding diacyl derivatives.

EXAMPLE 9

4-[2-(4-morpholinobutyryloxy)-4-(1,1-dimethylheptyl)-phenyl]-2-pentanone

Dicyclohexylcarbodiimide (0.227 g., 1.1 mmole) and 4-N-piperidylbutyric acid hydrochloride (0.222 g., 1.0 mmole) are added to a solution of 4-[4-(1,1-dimethylheptyl)-2-hydroxyphenyl]-2-pentanone (0.303 g., 1.0 mmole) in methylene chloride (25 ml.) at room temperature. The mixture is stirred for 18 hours and is then cooled to 0° C. and filtered. Evaporation of the filtrate affords the title product as its hydrochloride salt.

Similarly, the reactant of this example and the remaining phenolic compounds of this invention are converted to the basic esters of the phenolic hydroxy group by reaction with the appropriate basic reagent. Esters wherein the R$_1$ moiety has the following values are thus prepared:

—COCH$_2$NH$_2$
—CO(CH$_2$)$_2$N(C$_4$H$_9$)$_2$
—CO(CH$_2$)$_2$—N—(methyl)piperazino
—COC(CH$_3$)$_2$(CH$_2$)$_2$—piperidino
—CO(CH$_2$)$_3$N(C$_2$H$_5$)$_2$
—COCH(CH$_3$)(CH$_2$)$_2$—morpholino
—CO(CH$_2$)$_3$—pyrrolo
—CO(CH$_2$)$_3$—pyrrolidino
—COCH$_2$—pyrrolo
—CO(CH$_2$)$_3$—piperidino
—CO(CH$_2$)$_4$NH$_2$
—CO(CH$_2$)$_3$NH(C$_3$H$_7$)
—CO(CH$_2$)$_2$—N—butylpiperazino Careful neutralization of the hydrochloride salts affords the free basic esters which are converted to other acid addition salts according to the procedure of Example 10. In this manner, the hydrobromide, sulfate, acetate, malonate, citrate, glycolate, gluconate, succinate, sulfosalicylate and tartrate salts are prepared.

EXAMPLE 10

General Hydrochloride Salt Formation

Excess hydrogen chloride is passed into a solution of the appropriate compound of formulae I-II having a pyridyl group and the resulting precipitate separated and recrystallized from an appropriate solvent, e.g. methanol-ether (1:10).

The remaining compounds of formulae I-II which have a pyridyl group are converted to their hydrochlorides in like manner.

Similarly, the hydrobromide, sulfate, nitrate, phosphate, acetate, butyrate, citrate, malonate, maleate, fumarate, malate, glycolate, gluconate, lactate, salicylate, sulfosalicylate, succinate, pamoate, tartrate and embonate salts are prepared.

EXAMPLE 11

4[4-(1,1-Dimethylheptyl)-2-hydroxyphenyl]-2-butanol 2'-O-Hemisuccinate Ester Sodium Salt To a 0° C. solution of 1.00 g. (3.14 mmoles) of 4-[4-(1,1-dimethylheptyl)-2-hydroxyphenyl]-2-butanol in 3 ml. of dichloromethane is added 0.383 g. (3.14 mmoles) of 4-N,N-dimethylaminopyridine. To the resultant solution is slowly added 0.314 g. (3.14 mmoles) of succinic anhydride in one ml. of dichlormethane. The reaction mixture is stirred for 4 hours at 0° C. and then 3.14 ml. of 1N hydrochloric acid is slowly added. The reaction mixture is stirred 5 minutes longer and then added to 100 ml. water-100 ml. dichloromethane. The dichloromethane extract is dried over magnesium sulfate and evaporated. The residue is dissolved in 5 ml. of ethanol and 3.14 ml. of 1 N sodium hydroxide in ethanol added. Addition of ether causes crystallization. Recrystallization from ethanol-ether yields the title compound.

Replacement of sodium hydroxide by potassium hydroxide in the above procedure affords the potassium salt.

By means of this procedure, the remaining compounds described herein are converted to their hemisuccinate esters.

EXAMPLE 12

4-[4-(1,1-Dimethylheptyl)-2-hydroxyphenyl]-2-butanol 2'-O-Phosphate Ester Monosodium Salt To a 0° C. slurry of 0.126 g. (3.14 mmoles) of potassium hydride in 3 ml. of dimethylformamide is added a solution of 1.00 g. (3.14 mmoles) of 4-[4-(1,1-dimethylheptyl)-2-hydroxyphenyl]-2-butanol in 3 ml. of dimethylformamide. After gas evolution ceases (~10 min.) 0.932 g. (3.14 mmoles) of dibenzylphosphorochloridate is slowly added. The reaction mixture is stirred for one hour and then added to 200 ml. ether-100 ml. water. The ether extract is washed with two 100 ml. portions of water, dried over magnesium sulfate and evaporated to a residue. The residue is mixed with 1.0 g. of 5% platinum on carbon and 25 ml. of ethanol and stirred under one atmosphere of hydrogen for 3 hours. The reaction mixture is filtered through diatomaceous earth and 3.14 ml. of 1 N sodium hydroxide in ethanol slowly added to the filtrate. Addition of ether causes crystallization of the product. Recrystallization from ethanol then yields the title compound.

Similarly, the remaining compounds described herein are converted to their phosphate ester monosodium salts and, by replacement of sodium hydroxide with potassium hydroxide, to their corresponding potassium salts.

EXAMPLE 13

One hundred mg. of 4-[4-(1,1-dimethylheptyl)-2-hydroxyphenyl]-2-butanol are intimately mixed and ground with 900 mg. of starch. The mixture is then loaded into telescoping gelatin capsules such that each capsule contains 10 mg. of drug and 90 mg. of starch.

EXAMPLE 14

A tablet base is prepared by blending the ingredients listed below:
Sucrose: 80.3 parts
Tapioca starch: 13.2 parts
Magnesium Stearate: 6.5 parts
Sufficient trans-4-[4-(1,1-dimethylheptyl)-2-hydroxyphenyl]-2-butanone is blended into this base to provide tablets containing 0.5, 1, 5, 10 and 25 mg. of drug.

EXAMPLE 15

Suspensions of 4-[4-(1,1-dimethylheptyl)-2-hydroxyphenyl]-2-pentanone are prepared by adding sufficient amounts of drug to 0.5% methylcellulose to provide suspensions having 0.1, 0.5, 1, 5 and 10 mg. of drug per ml.

PREPARATION A 2-(3-Benzyloxyphenyl)-2-methylpropionitrile

To a solution of 1500 ml. of dimethylsulfoxide saturated with methyl bromide is simultaneously added a solution of 294 g. (1.32 mole) of 2-(3-benzyloxyphenyl)acetonitrile in 200 ml. dimethyl sulfoxide and a solution of 420 ml. of 50% aqueous sodium hydroxide. Methyl bromide is continuously bubbled through the reaction mixture during the above addition (30 minutes) and then for 1.5 hours longer while the reaction temperature is maintained at $\leq 50°$ C. with ice cooling. The reaction mixture is added to 2 liters of water-2 kg. ice and the resultant mixture extracted four times with 1 liter of ether. The combined ether extracts are washed twice with one liter of water, once with one liter of saturated sodium choride, dried over magnesium sulfate and evaporated to yield 325 g. (98%) of product as an oil.

PMR: $\delta_{CDCl_3}^{TMS}$ 1.70 (s, methyl), 5.12 (s, methylene), 6.8–7.5 (m, ArH) and 7.45 (s, PhH).

IR: (CHCl$_3$) 2247, 1616 and 1603 cm$^{-1}$.

MS: m/e 251 (M$^{30}$), 236, 160 and 91.

PREPARATION B 2-(3-Benzyloxyphenyl)-2-methylpropionaldehyde

To a 15° C. solution of 325 g. (1.25 mole) of 2-(3-benzyloxyphenyl)-2-methylpropionitrile in 1.85 liters of tetrahydrofuran is added 1.6 moles of diisobutylaluminum hydride as a 1.3 M solution in hexane (reaction temperature is maintained at 15°–18° C.). The reaction mixture is allowed to warm to room temperaure and is stirred 2 hours longer. It is then quenched by addition to a solution of 170 ml. of concentrated sulfuric acid in 670 ml. of water (temperature $\leq 30°$ C.). The resultant mixture is allowed to warm to room temperature and is then stirred an additional 2 hours. The organic layer is separated and the aqueous phase extracted once with one liter of ether. The combined organic phase is washed with 500 ml. of water and 500 ml. of saturated sodium chloride, dried over magnesium sulfate and evaporated to yield 315 g. (99%) of the title product.

PMR: $\delta_{CDCl_3}^{TMS}$ 1.43 (s, methyls), 5.08 (s, methylenes), 6.8–7.5 (m, ArH), 7.4 (s, PhH) and 9.55 (s, aldehyde).

PREPARATION C 2-(3-Benzyloxyphenyl)-2-methyl-cis-oct-3-ene

To a 15° C. solution of 1.8 moles of dimsyl sodium (from sodium hydride and dimethyl sulfoxide) in 2 liters of dimethyl sulfoxide is added, portionwise, 768 g. (1.8 moles) of pentyltriphenylphosphonium bromide. The resultant slurry is stirred 15 minutes at 15°–20° C. and then 315 g. (1.24 moles) of 2-(3-benzyloxyphenyl)-2-methylpropionaldehyde is slowly added (reaction temperature $\leq 30°$ C.). The resultant mixture is stirred for 4 hours at room temperature and is then added to 6 liters of ice water. The quenched reaction is extracted four times with one liter portions of 50% ether-pentane. The combined extract is washed twice with one liter of water and once with one liter of saturated sodium chloride and is then dried over magnesium sulfate and evaporated to yield an oil. Crystallization of this oil in 50% etherpentane (to remove triphenylphosphine oxide), filtration and evaporation of the filtrate gives 559 g. of oil. The crude oil is purified via column chromatography on 2 kg. of silica gel eluted with 20% hexane-dichloromethane to yield 217 g. (57%) of 2-(3-benzyloxyphenyl)-2-methyl-cis-oct-3-ene.

PMR: $\delta_{CDCl_3}^{TMS}$ 0.75 (bt, J=6Hz, terminal methyl), 1.1 (m, two side-chain methylenes), 1.43 (s, gem dimethyl), 1.60 (m, allylic methylene), 5.09 (s, benzylic methylene), 5.28 (dt, J=12 and 6 Hz, vinyl H), 5.70 (dd, J=12 and 1 Hz, vinyl H), 6.7–7.5 (m, ArH) and 7.42 (s, PhH).

IR: (CHCl$_3$) 1610 and 1587 cm$^{-1}$.

MS: m/e 308 (M+), 293, 274, 265, 251, 239, 225, 217 and 91.

similarly, 1-benzyloxy-3-(1,1-dimethyloct-2-enyl)benzene (13.5 g., 70%) is prepared from 15.75 g. (0.062 mol.) of 2-(3-benzyloxyphenyl)-2-methylpropionaldehyde and 37.5 g. (0.0899 mol.) of hexyltriphenylphosphonium bromide. The product is an oil.

PMR: $\delta_{CDCl_3}^{TMS}$ 0.78 (m, terminal sidechain methyl), 1.40 (s, gem dimethyl), 4.97 (s, benzyl ether methylene), 5.23 (m, vinyl H), 5.57 (d, J=11 Hz, vinyl H) and 6.6–7.4 (m, ArH and PhH).

IR: (CHCl$_3$) 1608 and 1583 cm$^{-1}$.

MS: m/e 322 (M+), 307, 279, 274, 265 and 231.

PREPARATION D 2-(3-Hydroxyphenyl)-2-methyloctane

A mixture of 65 g. (0.211 mole) of 2-(3-benzyloxyphenyl)-2-methyl-cis-oct-3-ene and 7.5 g. of 10% palladium-on-carbon in 100 ml. of ethanol is hydrogenated for one hour on a Parr apparatus at 50 p.s.i. hydrogen pressure. Additional 7.5 g. portions of 10% palladium-on-carbon are added after one and two hours of reaction and the reaction continued for 12 more hours. The reaction mixture is filtered through distomaceous earth with ethanol and the filtrate evaporated to an oil. The oil is purified via column chromatography on one kg. of silica gel eluted with 50% hexane-dichloromethane to yield 105 g. (78%) of 2-(3-hydroxyphenyl)-2-methyloctane.

PMR: $\delta_{CDCl_3}^{TMS}$ 0.85 (bt, terminal methyl), 1–1.9 (m, methylenes), 1.29 (s, gem dimethyl), 4.98 (s, phenol H) and 6.6–7.4 (m, ArH).

IR: (CHCl$_3$) 3571, 3311 and 1592 cm$^{-1}$.

MS: m/e 220 (M+), 205 and 135.

In like manner, 2-(3-hydroxyphenyl)-2-methylnonane is prepared in 82% (7.8 g.) yield from 13.0 g. (0.0406 mol.) of 1-benzyloxy-3-(1,1-dimethyl-oct-2-enyl)benzene. It is obtained as an oil having the characteristics:

PMR: $\delta_{CDCl_3}^{TMS}$ 0.85 (m, terminal methyl), 1.27 (s, gem dimethyl), 5.25 (bs, OH) and 6.6–7.4 (m, ArH).

IR: (CHCl$_3$) 3571, 3279, 1563 and 1527 cm$^{-1}$.

MS: m/e 234 (M+), 219, 191, 178, 164, 149, 135 and 121.

PREPARATION E

2-(4-Bromo-3-hydroxyphenyl)-2-methyloctane

To a 0° C. solution of 110 g. (0.50 mole) of 2-(3-hydroxyphenyl)-2-methyloctane in 200 ml. of carbon tetrachloride is added dropwise a solution of 80 g. (0.50 mole) of bromine in 90 ml. of carbon tetrachloride (reaction temperature ≦30° C. with cooling). The reaction mixture is stirred an additional 15 minutes and is then evaporated to yield 150 g. (100%) of 2-(4-bromo-3-hydroxyphenyl)-2-methyloctane.

PMR: $\delta_{CDCl_3}^{TMS}$ 0.85 (bt, terminal methyl), 0.8–1.9 (m, methylenes), 1.28 (s, gem dimethyl), 5.4 (bs, phenolic H), 6.78 (dd, J=8 and 2Hz, C-6 ArH), 7.02 (d, J=2Hz, C-2 ArH) and 7.37 (d, J=8Hz, C-5 ArH).

In like manner, 2-(4-bromo-3-hydroxyphenyl)-2-methylnonane is prepared in 82% (8.5 g.) yield as an oil from 7.8 g. (0.033 mol.) of 2-(3-hydroxyphenyl)-2-methylnonane:

PMR: $\delta_{CDCl_3}^{TMS}$ 0.86 (m, terminal methyl), 1.27 (s, gem dimethyl), 5.50 (bs, OH), 6.83 (dd, J=8 and 2Hz, ArH), 7.08 (d, J=2Hz, ArH) and 7.43 (d, J=8 Hz, ArH).

IR: (CHCl₃) 3279, 1613, and 1587 cm⁻¹.

MS: m/e 314, 312 (M+), 212, 210, 185 and 187.

PREPARATION F

2-(3Benzyloxy-4-bromophenyl)-2-methyloctane

To a −18° C. slurry of 23.0 g. (0.575 mole) of potassium hydride in 400 ml. of N,N-dimethylformamide is added over a 45 minute period a solution of 150 g. (0.5 mole) of 2-(4-bromo-3-hydroxyphenyl)-2-methyloctane in 400 ml. of N,N-dimethylformamide (reaction temperature ≦−15° C.). The reaction mixture is stirred 15 minutes longer after which a solution of 98.3 g. (0.575 mole) of benzyl bromide in 200 ml. of N,N-dimethylformamide is added. The mixture is then warmed to room temperature and stirred 30 minutes longer. It is quenched by addition to 6 liters of ice water. The quenched mixture is extracted six times with 500 ml. of ether. The combined extract is washed twice with one liter portions of water and once with one liter of saturated sodium chloride, dried over magnesium sulfate and evaporated to a quantitative yield of the title product.

PMR: $\delta_{CDCl_3}^{TMS}$ 0.85 (bt, terminal methyl), 0.8–2.0 (m, methylenes), 1.22 (s, gem dimethyl), 5.17 (s, benzylic methylene) and 6.7–7.6 (two multiplets, ArH and PhH).

IR: (CHCl₃) 1592 and 1575 cm⁻¹.

MS: m/e 390, 388, (M+), 375, 373, 354, 352, 305, 303 and 91.

And, 2-(3-benzyloxy-4-bromophenyl-2-methylnonane is prepared in 95% (10.4 g.) yield from 2-(3-hydroxy-4-bromophenyl)-2-methylnonane (8.5 g., 0.027 mol.), sodium hydride (0.744 g., 0.031 mol.) and benzyl bromide (5.3 g., 0.031 mol.) as an oil.

PMR: $\delta_{CDCl_3}^{TMS}$ 0.87 (terminal methyl), 1.23 (s, gem dimethyl), 5.18 (s, benzyl ether methylene), 6.8 (dd, J=8 and 2Hz, ArH), 6.97 (d, J=2Hz, ArH) and 7.43 (m, ArH and PhH).

IR: (CHCl₃) 1600 and 1575 cm⁻¹.

MS: m/e 404, 402 (M+), 305, 303, 91.

The compounds tabulated below are prepared according to the procedures of Preparations C-F from appropriate reactants:

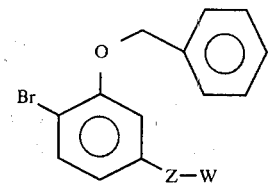

| Z | W |
|---|---|
| C(CH₃)₂(CH₂)₂ | H |
| C(CH₃)₂(CH₂)₁₀ | H |
| C(CH₃)₂(CH₂)₄ | C₆H₅ |
| C(CH₃)₂(CH₂)₄ | 4-pyridyl |
| C(CH₃)₂(CH₂)₃ | 2-pyridyl |
| C(CH₃)₂(CH₂)₁₀ | C₆H₅ |
| CH(CH₃)(CH₂)₂ | C₆H₅ |
| CH(C₂H₅)(CH₂)₂ | 4-ClC₆H₄ |
| CH(C₂H₅)(CH₂)₄ | 4-FC₆H₄ |
| (CH₂)₅ | H |
| (CH₂)₁₁ | H |
| (CH₂)₁₃ | H |
| (CH₂)₄ | C₆H₅ |
| (CH₂)₈ | H |

PREPARATION G

3-Benzyloxy-4-bromophenol

To a 0° C. slurry of 1.7 g. (42.5 mmoles) of potassium hydride in 35 ml of N,N-dimethylformamide is slowly added a solution of 7.22 g. (38.2 mmoles) of 4-bromoresorcinol. The resultant mixture is stirred for 30 minutes and then 4.54 ml. (38.2 mmoles) of benzyl bromide is slowly added. The reaction mixture is stirred 3 hours longer at 0° C. and then added to 200 ml. of cold water and 200 ml. of ether. The ether extract is washed twice with 200 ml. portions of water, dried over magnesium sulfate and evaporated to an oil. The crude oil is purified via column chromatography an 400 g. of silica gel eluted with 25% ether-pentane to yield (in order of elution) 2.2 g. (16%) of 2,4-dibenzyloxybromobenzene, 0.21 g. (2%) of 5-benzyloxy-2-bromophenol and 3.52 g. (33%) of 3-benzyloxy-4-bromophenol.

5-Benzyloxy-2-bromophenol

PMR: $\delta_{CDCl_3}^{TMS}$ 4.98 (s, benzyl ether), 5.46 (bs, OH), 6.40 (dd, J=8 and 2Hz, ArH), 6.60 (d, J=2Hz, ArH), 7.17 (d, J=8Hz, ArH) and 7.33 (s, PhH).

IR: (CDCl₃) 3521, 3221, 1610 and 1600 cm⁻¹.

MS: m/e 280, 278 (M+), 189, 187 and 91.

3-Benzyloxy-4-bromophenol

PMR: $\delta_{CDCl_3}^{TMS}$ 5.00 (s, benzyl ether methylene), 5.33 (bs, OH), 6.21 (dd, J=8 and 2Hz, ArH), 6.38 (d, J=2Hz, ArH) and 7.30 (m, ArH and PhH).

IR: (CHCl₃) 3546, 3257, 1603 and 1585 cm⁻¹.

MS: m/e 280, 278 (M+) and 91.

PREPARATION H

2-Benzyloxy-4-[2-(5-phenylpentyloxy)]bromobenzene

A mixture of 3.50 g. (12.5 mmoles) of 3-benzyloxy-4-bromophenol, 3.48 g. (14.4 mmoles) of 2-(5-phenylpentyl)methanesulfonate and 5.17 g. (37.5 mmoles) of anhydrous potassium carbonate in 20 ml. of N,N-dimethylformamide is heated at 85° C. for 6 hours. It is then closed and added to 200 ml. of water and 200 ml. of ether. The organic extract is washed twice with 150 ml. portions of water, dried over magnesium sulfate and evaporated to an oil. The oil is purified via column chromatography on 400 g. of silica gel eluted with 2:1 pentane:methylene chloride to yield 4.39 g. (82%) of the desired product as an oil.

PMR: $\delta_{CDCl_3}{}^{TMS}$ 1.21 (d, J=6Hz, sidechain methyl), 1.7 (m, sidechain methylenes), 2.60 (m, sidechain benzyl methylene), 4.25 (m, sidechain methine), 5.00 (s, benzyl ether methylene), 6.22 (dd, J=8 and 2Hz, C-5 ArH), 6.39 (d, J=2Hz, C-3 ArH) and 7.30 (m, PhH and C-6 ArH).

IR: (CHCl$_3$) 1587 cm$^{-1}$. MS: 426, 424 (M+), 280, 278 and 91.

The following compounds are similarly prepared from the appropriate mesylate CH$_3$SO$_3$—Z—W.

| (alk$_2$) | W |
| --- | --- |
| (CH$_2$)$_4$ | 4-FC$_6$H$_4$ |
| (CH$_2$)$_8$ | C$_6$H$_5$ |
| (CH$_2$)$_{10}$ | 4-ClC$_6$H$_4$ |
| CH(CH$_3$)(CH$_2$)$_8$ | C$_6$H$_5$ |
| CH(CH$_3$)CH$_2$ | 4-FC$_6$H$_4$ |
| C(CH$_3$)$_2$(CH$_2$)$_3$ | C$_6$H$_5$ |
| CH$_2$CH(CH$_3$)CH$_2$ | C$_6$H$_5$ |
| CH(CH$_3$)(CH$_2$)$_{10}$ | H |
| C(CH$_3$)$_2$(CH$_2$)$_5$ | H |
| C(CH$_3$)$_2$(CH$_2$)$_7$ | H |
| (CH$_2$)$_{13}$ | H |
| (CH$_2$)$_{13}$ | C$_6$H$_5$ |
| CH(CH$_3$)(CH$_2$)$_6$ | 4-FC$_6$H$_4$ |
| C(CH$_3$)$_2$(CH$_2$)$_{10}$ | 4-FC$_6$H$_4$ |
| (CH$_2$)$_{12}$ | C$_6$H$_5$ |
| CH(C$_2$H$_5$)(CH$_2$)$_3$ | 4-ClC$_6$H$_4$ |
| C(CH$_3$)$_2$(CH$_2$)$_6$ | H |
| (CH$_2$)$_2$C(CH$_3$)$_2$(CH$_2$)$_2$ | H |
| (CH$_2$)$_6$ | C$_6$H$_5$ |
| (CH$_2$)$_{12}$ | H |
| CH(CH$_3$)(CH$_2$)$_3$ | 4-pyridyl |
| (CH$_2$)$_2$ | 4-pyridyl |
| CH(CH$_3$)(CH$_2$)$_3$ | 2-pyridyl |
| (CH$_2$)$_5$ | 3-pyridyl |
| (CH$_2$)$_{10}$ | 2-pyridyl |
| CH(C$_2$H$_5$)(CH$_2$)$_2$ | 4-pyridyl |

PREPARATION I

1Bromo-2,4-dibenzyloxybenzene

A mixture of 75.0 g. (0.397 mol.) of 4-bromoresorcinol, 95.1 ml. (0.80 mol) of benzylbromide and 331 g. (2.4mol.) of anhydrous potassium carbonate in 400 ml. of N,N-dimethylformamide is stirred for 12 hours at 25° C. and for 4 hours at 85° C. The reaction mixture is cooled and added to one liter of ice-200 ml. pentane-100 ml. ether. The organic phase is washed with three 500 ml. portions of water, dried over magnesium sulfate and evaporated to an oil. The oil is rapidly chromatographed on 400 g. of silica gel eluted with 20% etherpentane to yield 80 g of oil. The chromatographed oil is crystallized from pentane at 0° C. to yield 45.0 g. (30%) of the title compound, M.P. 37°–38° C.

PMR: $\delta_{CDCl_3}{}^{TMS}$ 5.0 (s, C-4 benzylether methylene), 5.08 (s, C-2 benzylether methylene), 6.45 (dd, J=8 and 2Hz, C-5H), 6.63 (d, J=2Hz, C-3H), 7.2–7.6 (m, PhH and ArH).

IR: (CHCl$_3$) 1605 and 1590 cm$^{-1}$.
MS: m/e 370 (M+), 368 and 91.
Analysis: Anal. Calc'd for C$_{20}$H$_{17}$BrO$_2$: C, 65.03; H, 4.64; Br, 21.65. Found: C, 64.95; H, 4.55; Br, 21.48.

PREPARATION J 2-(3-Methoxyphenyl)-5-phenylpentane

A solution of 1-bromopropylbenzene (51.7 g.) in ether (234 ml.) is added dropwise over a 2-hour period to a refluxing mixture of magnesium (7.32 g.) in ether (78 ml.). The reaction mixture is refluxed for 30 minutes longer and then a solution of 3-methoxy-acetophenone (41.6 g.) in ether (78 ml.) is added dropwise and the mixture heated to reflux for 1.5 hours. The reaction is quenched by addition of saturated ammonium chloride (234 ml.), the ether layer is separated and the aqueous phase extracted with ether (3×200 ml.). The combined ether extracts are dried over magnesium sulfate and concentrated under vacuum to yield an oil. The oil is hydrogenated in a mixture containing ethanol (300 ml.), concentrated hydrochloric acid (2 ml.) and 5% palladium-on-carbon (5 g.). The catalyst is filtered off and the ethanol removed under vacuum. The residue is distilled under vacuum to give the title product.

PREPARATION K 2-(3-Hydroxyphenyl)-5-phenylpentane

A mixture of 2-(3-methoxyphenyl)-5-phenylpentane (18.4 g.) and pyridine hydrochloride (94 g.) under nitrogen is heated to 190° C. for 2 hours with vigorous stirring. The reaction mixture is cooled, dissolved in 6N hydrochloric acid (200 ml.) and diluted with water to 600 ml. The aqueous solution is extracted with ethyl acetate (4×100 ml.), the ethyl acetate extracts dried over sodium sulfate and concentrated under vacuum to yield the crude product. The product is purified by silica gel chromatography.

The following compounds are prepared from appropriate reactants by the method of Preparation J and that of the above preparation:

| Z | W |
| --- | --- |
| CH(CH$_3$)(CH$_2$)$_2$ | C$_6$H$_5$ |
| CH(C$_2$H$_5$)(CH$_2$)$_2$ | 4-ClC$_6$H$_4$ |
| CH(C$_2$H$_5$)(CH$_2$)$_4$ | 4-FC$_6$H$_4$ |
| (CH$_2$)$_5$ | H |
| (CH$_2$)$_{11}$ | H |
| (CH$_2$)$_{13}$ | H |
| (CH$_2$)$_4$ | C$_6$H$_5$ |
| (CH$_2$)$_8$ | H |

Bromination of the above compounds according to the procedure of Preparation E affords the corresponding 4-bromo derivatives, e.g. 2-(4-bromo-3-hydroxyphenyl)-5-phenylpentane.

PREPARATION L

Ethyl 3-(3-Benzyloxyphenyl)crotonate (Wittig Reaction)

A mixture of 3-benzyloxyacetophenone (29.4 g., 0.13 mole) and carbethoxymethylenetriphenylphosphorane (90.5 g., 0.26 mole) is heated under a nitrogen atmosphere at 170° C. for 4 hours. The clear melt is cooled to room temperature, triturated with ether and the precipitate of triphenyl phosphine oxide removed by filtration. The filtrate is concentrated under vacuum to an oily residue which is chromatographed over silica gel (1500 g.) and eluted with benzene:hexane solutions of increasing benzene concentration beginning with 40:60 and ending with 100% benzene. Concentration of appropriate fractions gives the product as an oily residue.

PREPARATION M

3-(3-Benzyloxyphenyl)butyl Tosylate

A solution of ethyl 3-(3-benzyloxyphenyl)crotonate (17.8 g., 60 mmole) in ether (250 ml.) is added to a mixture of lithium aluminum hydride (3.42 g., 90 mmole) and ether (250 ml.). Aluminum chloride (0.18 g., 1.35 mmole) is added and the mixture refluxed for 12 hours and then cooled. Water (3.4 ml.), sodium hydroxide (3.4 ml. of 6N) and water (10 ml.) are then added successively to the reaction mixture. The inorganic salts which precipitate are filtered off and the filtrate is then concentrated in vacuo to give the 3-(3-benzyloxyphenyl)butanol as an oil.

Tosyl chloride (11.1 g., 58.1 mmole) is added to a solution of 3-(3-benzyloxyphenyl)-1-butanol (14.5 g., 57 mmole) in pyridine (90 ml.) at −45° C. The reaction mixture is held at −35° C. for 18 hours and is then diluted with cold 2N hydrochloric acid (1500 ml.) and extracted with ether (5×200 ml.). The combined extracts are washed with saturated sodium chloride solution (4×250 ml.) and then dried (Na$_2$SO$_4$). Concentration of the dried extract affords the product as an oil.

PREPARATION N

3-(3-Benzyloxyphenyl)-1-phenoxybutane

A solution of phenol (4.56 g., 48.6 mmole) in dimethylformamide (40 ml.) is added under a nitrogen atmosphere to a suspension of sodium hydride (2.32 g., 48.6 mmole) of 50% previously washed with pentane) in dimethylformamide (70 ml. at 60° C. The reaction mixture is stirred for one hour at 60°–70° C., after which a solution of 3-(3-benzyloxyphenyl)butyl tosylate (18.9 g., 46 mmole) in dimethylformamide (80 ml.) is added. The reaction mixture is stirred at 80° C. for a half hour and is then cooled to room temperature, diluted with cold water (2500 ml.) and extracted with ether (4×400 ml.). The combined extracts are washed successively with cold 2 N hydrochloric acid (2×300 ml.) and saturated sodium chloride solution (3×300 ml.) and then dried (Na$_2$SO$_4$). Removal of the solvent under reduced pressure affords the product as an oil. The oil residue is dissolved in benzene and filtered through silica gel (100 g.). Concentration of the filtrate under reduced pressure gives the product as an oil.

Repetition of Preparations L through N but using the 3-benzyloxy derivatives of benzaldehyde, acetophenone or propiophenone, the appropriate carbethoxy (or carbomethoxy) alkylidenetriphenylphosphorane, and the appropriate alcohol or phenol affords the following compounds.

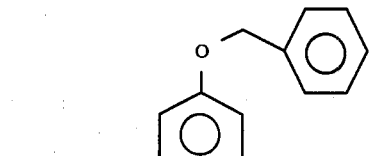

(alk$_1$)-O—(alk$_2$)$_n$-W

| (alk$_1$) | n | (alk$_2$) | W |
|---|---|---|---|
| (CH$_2$)$_3$ | 1 | (CH$_2$)$_3$ | H |
| (CH$_2$)$_3$ | 1 | (CH$_2$)$_5$ | H |
| (CH$_2$)$_5$ | 1 | (CH$_2$)$_8$ | H |
| (CH$_2$)$_6$ | 1 | (CH$_2$)$_7$ | H |
| (CH$_2$)$_3$ | 1 | (CH$_2$)$_7$ | H |
| (CH$_2$)$_3$ | 1 | (CH$_2$)$_{10}$ | H |
| (CH$_2$)$_{10}$ | 1 | (CH$_2$)$_2$ | H |
| C(CH$_3$)$_2$(CH$_2$)$_2$ | 1 | (CH$_2$)$_4$ | H |
| (CH$_2$)$_4$ | 1 | CH$_2$ | C$_6$H$_5$ |
| (CH$_2$)$_6$ | 0 | — | C$_6$H$_5$ |
| (CH$_2$)$_{13}$ | 0 | — | H |
| (CH$_2$)$_6$ | 0 | — | H |
| (CH$_2$)$_6$ | 1 | CH$_2$ | 4-ClC$_6$H$_4$ |
| (CH$_2$)$_6$ | 0 | — | 4-FC$_6$H$_4$ |
| CH(CH$_3$)(CH$_2$)$_2$ | 0 | — | C$_6$H$_5$ |
| CH(CH$_3$)(CH$_2$)$_3$ | 0 | — | C$_6$H$_5$ |
| CH(CH$_3$)(CH$_2$)$_6$ | 0 | — | H |
| (CH$_2$)$_3$ | 0 | — | 4-pyridyl |
| (CH$_2$)$_3$ | 0 | — | 3-pyridyl |
| (CH$_2$)$_3$ | 1 | CH(CH$_3$) | 2-pyridyl |
| CH(CH$_3$)(CH$_2$)$_2$ | 1 | (CH$_2$)$_4$ | 4-pyridyl |
| CH(C$_2$H$_5$)(CH$_2$)$_2$ | 1 | CH(CH$_3$) | 2-pyridyl |
| (CH$_2$)$_4$ | 1 | (CH$_2$)$_5$ | 4-pyridyl |
| (CH$_2$)$_8$ | 1 | (CH$_2$)$_5$ | 4-pyridyl |

Bromination of the products according to the procedure of Preparation E affords the corresponding 2-bromo-5-[(alk$_1$)-O-(alk$_2$)$_n$-W]-phenolbenzyl ethers.

PREPARATION O

4-(3-Hydroxyphenyl)-1-(4-pyridyl)pentane

A mixture of 3-(3-methoxyphenyl)butyl triphenylphosphonium bromide (17.5 g., 35.4 mmoles) in dimethylsulfoxide (50 ml.) is added to 4-pyridinecarboxaldehyde (3.79 g., 35.4 mmoles) in tetrahydrofuran (40 ml.). The resulting mixture is then added dropwise to a slurry of 50% sodium hydride (1.87 g., 39 mmoles) in tetrahydrofuran (20 ml.) under a nitrogen atmosphere at 0°–5° C. Following completion of addition, the mixture is stirred for one hour at 0°–5° C. and then concentrated under reduced pressure. The concentrate is diluted with water (200 ml.) and then acidified with 6 N HCl. The aqueous acid solution is extracted with benzene (4×50 ml.) It is then made basic and extracted with ethyl acetate (3×50 ml.). Evaporation of the combined extracts after drying (MgSO$_4$) affords 4-(3-methoxyphenyl)-1-(4-pyridyl)-1-pentene as an oil.

Catalytic hydrogenation of the thus-produced pentene derivative in ethanol at 45 p.s.i. in the presence of Pd/C (1 g. of 10%) and concentrated HCl (1 ml.) affords the title product.

The pentane derivative thus obtained is demethylated by heating a mixture of the compound (25 mmoles) and pyridine hydrochloride (35 g.) under a nitrogen atmosphere at 210° C. for 8 hours. The hot mixture is poured into water (40 ml.) and the resulting solution made basic with 6 N sodium hydroxide. Water and pyridine are removed by distillation in vacuo. Ethanol (50 ml.) is added to the residue and the inorganic salts which precpitate are filtered off. The filtrate is concentrated in vacuo and the residue chromatographed on silica gel using as eluting agents 5% ethanol/benzene (4 liters), 10% ethanol/benzene (1 liter), 13% ethanol/benzene (1 liter), and 16% ethanol/benzene (5 liters). The product is isolated by concentration of appropriate fractions of the eluate.

The 3-(3-methoxyphenyl)butyltriphenylphosphonium bromide is prepared by refluxing a mixture of 1-bromo-3-(3-methoxyphenyl)butane (78.5 mmoles) and triphenyl phosphine (78.5 mmoles) in xylene (60 ml.) for 18 hours. The reaction mixture is then cooled to room temperature and filtered. The filter cake is washed with ether and the product dried in a vacuum desiccator.

Repetition of this procedure but using the appropriate bromo-(3-methoxyphenyl)alkane and the appropriate aldehyde or ketone affords the following compounds.

OH–C₆H₃(Z–W) structure (3-substituted phenol)

| Z | W |
| --- | --- |
| (CH$_2$)$_3$ | 2-pyridyl |
| (CH$_2$)$_4$ | 4-pyridyl |
| CH(CH$_3$)CH(CH$_3$)CH$_2$ | 3-pyridyl |
| CH(CH$_3$)CH(CH$_3$)CH$_2$ | 4-pyridyl |
| CH(C$_2$H$_5$)(CH$_2$)$_2$ | 4-pyridyl |
| (CH$_2$)$_{10}$ | 4-pyridyl |

Bromination of the above compounds according to the method of Preparation E gives the corresponding 2-bromo-5-(Z-W)-phenols.

PREPARATION P

3-Methoxy-α-methylstyrene Oxide

To a solution of dimethylsulfoxonium methylide (69.4 mmoles) in dimethyl sulfoxide (65 ml.) at room temperature is added solid 3-dimethoxyacetophenone (8.33 g., 55.5 mmoles). The reaction mixture is stirred for one hour at 25° C., for one-half hour at 50° C. and is then cooled. The mixture is diluted with water (50 ml.) and added to a mixture of ice water (200 ml.)—ether (250 ml.)—low boiling petroleum ether (25 ml.). The organic extract is washed twice with water (250 ml.), dried (MgSO$_4$) and evaporated to an oil which is fractionally distilled.

PREPARATION Q

2-(3-Methoxyphenyl)-2-hydroxypropyl-2-phenylethyl Ether

A mixture of dry 2-phenylethanol (30 ml., 251 mmoles) and sodium metal (690 mg., 30 mmoles) is heated at 110° C. for 30 minutes. The resulting 1 M solution of sodium 2-phenylethoxide is cooled to 60° C., 3-methoxy-α-methylstyrene oxide (1.69 g., 10.3 mmoles) added and the reaction heated 15 hours at 60° C. The reaction mixture is cooled and added to a mixture of ether and water. The ether extract is dried over magnesium sulfate and evaporated. Excess 2-phenylethanol is removed by vacuum distillation (b.p. ~65° C., 0.1 mm.). The residue is purified via column chromatography on silica gel 60 (300 g.) and eluted in 15 ml. fractions with 60% ether-pentane.

PREPARATION R

2-(3-Methoxyphenyl)propyl 2-Phenylethyl Ether

To a 0° C. solution of 2-(3-methoxyphenyl)-2-hydroxypropyl 2-phenylethyl ether (498 mg., 1.74 mmole) in pyridine (2 ml.) is added dropwise phosphorous oxychloride (477 μl., 5.22 mmole). The reaction is allowed to warm to 20° C. over a 1.5 hour period. It is then stirred for 1.5 hours at 20° C. and then added to ether (150 ml.) and 15% sodium carbonate (100 ml.). The organic phase is separated and washed with 15% sodium carbonate (3×50 ml.), dried over magnesium sulfate and evaporated to an oil. The oil is dissolved in absolute ethanol (15 ml.), 10% palladium-on-carbon (100 mg.) added and the mixture stirred under one atmosphere of hydrogen gas. When hydrogen uptake ceases the reaction is filtered through diatomaceous earth and the filtrate evaporated to an oil. The oil is purified via preparative layer chromatography on silica gel plates, eluted twice with 6:1 pentane:ether to yield the title compound.

PREPARATION S

2-(3-Hydroxyphenyl)propyl 2-Phenylethyl Ether

A mixture of 2-(3-methoxyphenyl)propyl 2-phenylethyl ether (176 mg., 0.65 mmole), pyridine (0.4 ml., 4.96 mmole) and dry pyridine hydrochloride (4 g., 34.6 mmole) is heated at 190° C. for 6 hours. The reaction mixture is cooled and added to a mixture of water (100 ml.) and ether (150 ml.). The ether extract is washed once with water (50 ml.) and, along with a second ether extract (50 ml.) of the aqueous phase, is dried over magnesium sulfate and evaporated to an oil. The oil is purified via preparative layer chromatography on silica gel plates, eluted six times with 30% ether-pentane to yield the title product.

The following compounds are prepared from appropriate alkanols by the methods of Procedures Q and R:

3-HO-C$_6$H$_4$-CH(CH$_3$)-CH$_2$-O-(alk$_2$)-W

| (alk$_2$) | W |
| --- | --- |
| —(CH$_2$)$_7$— | H |
| —(CH$_2$)$_6$— | C$_6$H$_5$ |
| —(CH$_2$)$_5$— | H |
| —CH(CH$_3$)CH$_2$— | H |
| —CH(CH$_3$)(CH$_2$)$_5$— | H |
| —(CH$_2$)— | 4-FC$_6$H$_4$ |
| —(CH$_2$)$_2$— | 4-pyridyl |
| —(CH$_2$)$_2$— | 4-ClC$_6$H$_4$ |
| —(CH$_2$)$_2$CH(CH$_3$)(CH$_2$)$_3$— | H |
| —CH(CH$_3$)CH$_2$— | H |
| —C(CH$_3$)$_2$CH$_2$— | H |
| —(CH$_2$)$_{10}$— | H |
| —CH$_2$— | C$_6$H$_5$ |

PREPARATION T

3-Methoxy-β-methylstyrene Oxide

To a −78° C. solution of diphenylsulfonium ethylide (1.0 mole) in tetrahydrofuran (one liter) is slowly added 3-methoxybenzaldehyde (1.0 mole). The reaction mixture is stirred at −78° C. for 3 hours and then allowed to warm to room temperature. It is then added to ether-water and the ether phase separated. The ether phase is washed with water, dried (MgSO₄) and evaporated. Fractional distillation of the residue gives the title product.

PREPARATION U

3-(3-Hydroxyphenyl)-2-propylbutyl Ether

To a solution of sodium butoxide in butanol (0.5 liters of 1M) is added 3-methoxy-β-methylstyrene oxide (6.33 mole). The mixture is heated for 18 hours at 70° C. and is then cooled and added to a mixture of ether-water. The ether solution is separated, dried (MgSO₄) and evaporated to give the crude product 2-(3-methoxyphenyl)-3-hydroxy-2-propylbutyl ether. It is purified by column chromatography on silica gel with ether-pentane elution.

By means of the procedure of Preparation R the title product is produced.

Similarly, the following are prepared from appropriate alcohols:

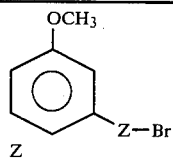

| (alk₂) | W |
|---|---|
| (CH₂)₂ | H |
| (CH₂)₇ | H |
| (CH₂)₃ | C₆H₅ |
| (CH₂)₂ | 4-FC₆H₄ |
| (CH₂)₂ | 4-pyridyl |
| CH(CH₃)(CH₂)₂ | H |
| CH(C₂H₅)(CH₂)₃ | H |
| CH(CH₃)CH₂ | C₆H₅ |
| CH₂ | H |
| (CH₂)₂ | 4-ClC₆H₄ |

PREPARATION V

1-Bromo-3-(3-methoxyphenyl)butane

A solution of phosphorous tribromide (5.7 ml., 0.06 mole) in ether (30 ml.) is added to a solution of 3-(3-methoxyphenyl)-1-butanol (30.0 g., 0.143 mole) in ether (20 ml.) at −5° C. to −10° C. and the reaction mixture stirred at −5° C. to −10° C. for 2.5 hours. It is then warmed to room temperature and stirred for an additional 30 minutes. The mixture is poured over ice (200 g.) and the resulting mixture extracted with ether (3×50 ml.). The combined extracts are washed with 5% sodium hydroxide solution (3×50 ml.), saturated sodium chloride solution (1×50 ml.) and dried (Na₂SO₄). Removal of the ether and vacuum distillation of the residue affords the title product.

The following compounds are prepared from 3-methoxybenzaldehyde, 3-methoxyacetophenone and 3-methoxypropiophenone and the appropriate carbethoxyalkylidene triphenylphosphorane by the procedures of Preparations L, M and the above procedure.

(CH₂)₃
(CH₂)₄
CH(C₂H₅)CH₂
CH(CH₃)CH₂
CH(CH₃)(CH₂)₃

PREPARATION W

β-(2-Pyridyl)vinyl phenyl ketone

A slurry of sodium hydride (50%, 2.4 g., 0.05 mole) in 100 ml. of dry 1,2-dimethoxyethane is cooled to 20° C. and diethyl phenacylphosphonate (11.4 g., 0.05 mole) added dropwise with stirring. The mixture is stirred at room temperature until gas evolution ceases. Then, 2-pyridinecarboxaldehyde (5.36 g., 0.05 mole) is added dropwise at 20° C. The mixture is stirred for one hour at 20°–25° C. and then refluxed for one hour. It is then cooled, a large excess of water added and the product extracted with ether. The extract is dried (MgSO₄) and evaporated to give the product.

By means of this procedure, the following α,β-unsaturated ketones and are prepared from appropriate dialkyl (dimethyl or diethyl) acyl phosphonates [(CH₃O)₂P(O)—CH₂COR₄] and appropriate aldehydes or ketones (R₂R₃CO).

| R₄—CO—CH=CR₂R₃ | | |
|---|---|---|
| R₂ | R₃ | R₄ |
| H | H | 2-pyridyl |
| H | H | 3-pyridyl |
| H | H | 4-pyridyl |
| H | H | CH₂C₆H₅ |
| H | H | (CH₂)₄C₆H₅ |
| CH₃ | H | 4-pyridyl |
| n-C₄H₉ | H | 4-pyridyl |
| n-C₃H₇ | H | 4-pyridyl |
| n-C₆H₁₃ | H | 4-pyridyl |
| CH₃ | H | 2-pyrdiyl |
| i-C₆H₁₃ | H | 2-pyridyl |
| CH₃ | H | 3-pyrdiyl |
| n-C₅H₁₁ | H | 3-pyridyl |
| C₆H₅ | H | 2-pyridyl |
| C₆H₅ | H | 3-pyridyl |
| C₆H₅ | H | 4-pyridyl |
| CH₂C₆H₅ | H | 4-pyridyl |
| (CH₂)₃C₆H₅ | H | 4-pyridyl |
| CH₂C₆H₅ | H | 3-pyridyl |
| CH₂C₆H₅ | H | 2-pyridyl |
| (CH₂)₄C₆H₅ | H | 2-pyridyl |
| 4-pyridyl | H | 4-pyridyl |
| 4-pyridyl | H | 2-pyridly |
| 2-pyridyl | H | 2-pyridyl |
| 4-pyridyl | H | 3-pyridyl |
| 4-pyridyl | H | H |
| 2-pyridyl | H | H |
| 3-pyridyl | H | H |
| C₆H₅ | H | CH₂C₆H₅ |
| 4-pyridyl | H | C₆H₅ |
| 3-pyridyl | H | C₆H₅ |
| 2-pyridyl | H | C₆H₅ |
| 4-pyridyl | H | CH₃ |
| 4-pyridyl | H | n-C₃H₇ |
| 4-pyridyl | H | i-C₆H₁₃ |
| 2-pyridyl | H | CH₃ |
| 2-pyridyl | H | n-C₄H₉ |
| 3-pyridyl | H | n-C₃H₇ |
| 3-pyridyl | H | CH₂C₆H₅ |

-continued

| $R_2$ | $R_4$—CO—CH=CR$_2$R$_3$ $R_3$ | $R_4$ |
|---|---|---|
| 4-pyridyl | H | CH$_2$C$_6$H$_5$ |
| 4-pyridyl | H | (CH$_2$)$_4$C$_6$H$_5$ |
| 2-pyridyl | H | (CH$_2$)$_3$C$_6$H$_5$ |
| H | H | C$_6$H$_5$ |
| CH$_2$C$_6$H$_5$ | H | CH$_2$C$_6$H$_5$ |
| CH$_2$C$_6$H$_5$ | H | (CH$_2$)$_3$C$_6$H$_5$ |
| (CH$_2$)$_4$C$_6$H$_5$ | H | CH$_2$C$_6$H$_5$ |
| CH$_2$C$_6$H$_5$ | H | C$_6$H$_5$ |
| (CH$_2$)$_3$C$_6$H$_5$ | H | C$_6$H$_5$ |
| CH$_2$C$_6$H$_5$ | H | CH$_3$ |
| (CH$_2$)$_4$C$_6$H$_5$ | H | CH$_3$ |
| CH$_2$C$_6$H$_5$ | H | n-C$_6$H$_{13}$ |
| CH$_3$ | H | CH$_2$C$_6$H$_5$ |
| n-C$_4$H$_9$ | H | CH$_2$C$_6$H$_5$ |
| CH$_3$ | H | (CH$_2$)$_4$C$_6$H$_5$ |
| n-C$_6$H$_{13}$ | H | (CH$_2$)$_4$C$_6$H$_5$ |
| n-C$_5$H$_{11}$ | H | n-C$_6$H$_{13}$ |
| i-C$_6$H$_{13}$ | H | CH$_3$ |
| n-C$_6$H$_{13}$ | H | n-C$_6$H$_{13}$ |
| CH$_3$ | CH$_3$ | CH$_3$ |
| n-C$_4$H$_9$ | CH$_3$ | CH$_3$ |
| CH$_3$ | CH$_3$ | n-C$_4$H$_9$ |
| CH$_3$ | CH$_3$ | n-C$_6$H$_{13}$ |
| C$_6$H$_5$ | CH$_3$ | CH$_3$ |
| t-C$_4$H$_9$ | CH$_3$ | CH$_3$ |
| CH$_3$ | CH$_3$ | C$_6$H$_5$ |
| CH$_3$ | CH$_3$ | CH$_2$C$_6$H$_5$ |
| C$_2$H$_5$ | CH$_3$ | CH$_2$C$_6$H$_5$ |
| CH$_3$ | CH$_3$ | (CH$_2$)$_3$C$_6$H$_5$ |
| n-C$_6$H$_{13}$ | CH$_3$ | CH$_2$C$_6$H$_5$ |
| CH$_3$ | CH$_3$ | 4-pyridyl |
| n-C$_4$H$_9$ | CH$_3$ | 4-pyridyl |
| i-C$_6$H$_{13}$ | CH$_3$ | 2-pyridyl |
| CH$_3$ | CH$_3$ | 2-pyridyl |
| C$_6$H$_5$ | CH$_3$ | 4-pyridyl |
| 4-pyridyl | CH$_3$ | C$_6$H$_5$ |
| 4-pyridyl | CH$_3$ | 4-pyridyl |
| CH$_2$C$_6$H$_5$ | CH$_3$ | 2-pyridyl |
| C$_6$H$_5$ | CH$_3$ | n-C$_5$H$_{11}$ |
| CH$_3$ | CH$_3$ | (CH$_2$)$_3$C$_6$H$_5$ |
| C$_6$H$_5$ | CH$_3$ | CH$_2$C$_6$H$_5$ |
| i-C$_3$H$_7$ | H | CH$_3$ |
| i-C$_3$H$_7$ | H | C$_2$H$_5$ |

What is claimed is:

1. A compound having the formula

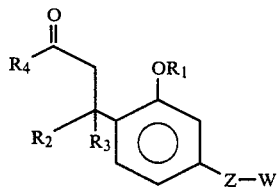

wherein

R$_1$ is selected from the group consisting of hydrogen, benzyl, alkanoyl having from one to five carbon atoms, —P(O)(OH)$_2$ and the sodium and potassium salts thereof, —CO(CH$_2$)$_2$COOH and the sodium and potassium salts thereof, and —CO—(CH$_2$)$_p$—NR$_5$R$_6$ wherein p is 0 or an integer from 1 to 4;

each of R$_5$ and R$_6$ when taken individually is selected from the group consisting of hydrogen and alkyl having from one to four carbon atoms; R$_5$ and R$_6$ when taken together with the nitrogen to which they are attached form a 5- or 6-membered heterocyclic ring selected from the group consisting of piperidino, pyrrolo, pyrrolidino, morpholino and N-alkylpiperazino having from one to four carbon atoms in the alkyl group;

each of R$_2$ and R$_4$ is selected from the group consisting of hydrogen, alkyl having from one to six carbon atoms, phenyl, pyridyl and phenylalkyl having from one to four carbon atoms in the alkyl moiety;

R$_3$ is selected from the group consisting of hydrogen and methyl;

Z is selected from the group consisting of (a) alkylene having from one to thirteen carbon atoms; (b) —(alk$_1$)$_m$—O—(alk$_2$)$_n$—wherein each of (alk$_1$) and (alk$_2$) is alkylene having from one to thirteen carbon atoms, with the proviso that the summation of carbon atoms in (alk$_1$) plus (alk$_2$) is not greater than thirteen; each of m and n is 0 or 1; and W is selected from the group consisting of hydrogen, pyridyl,

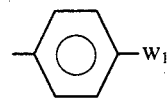

wherein W$_1$ is selected from the group consisting of hydrogen, fluoro and chloro;

and the pharmaceutically acceptable acid addition salts of those compounds wherein R$_1$ is —CO—(CH$_2$)$_p$—NR$_5$R$_6$ and/or R$_2$, R$_4$ or W is pyridyl;

and the hemiketals of those compounds wherein R$_1$ is hydrogen.

2. A compound according to claim 1 wherein R$_1$ is hydrogen and Z is alkylene.

3. A compound according to claim 2 wherein Z is alkylene having from 5 to 9 carbon atoms, each of R$_2$ and R$_4$ is alkyl and R$_3$ is hydrogen.

4. The compound having the formula

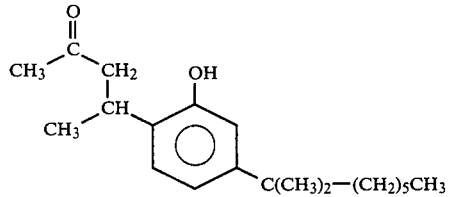

said compound being 4-[4-(1,1-dimethylheptyl)-2-hydroxyphenyl]-2-pentanone.

* * * * *

UNITED STATES PATENT AND TRADEMARK OFFICE
CERTIFICATE OF CORRECTION

PATENT NO. : 4,284,829

DATED : August 18, 1981

INVENTOR(S) : Thomas H. Althuis et al.

It is certified that error appears in the above-identified patent and that said Letters Patent are hereby corrected as shown below:

On The Title Page:

Abstract, line 1 below the formulae, "$C_1 14$" should read -- $C_1-$ --.

Col. 2, line 52, delete "fluoro and chloro" and insert -- pyridyl, --.

Col. 2, line 60, "$w_1$" should read -- $W_1$ --.

Col. 2, line 61, "hydrogen fluoro" should read -- hydrogen, fluoro --.

Col. 6, line 12, "acetaphenone" should read -- acetophenone --.

Col. 6, line 14, after "group" insert -- are --.

Col. 6, line 19, "$(C_6H_5)_3P + C(R^1)-COOC_2H_5$" should read -- $(C_6H_5)_3P=C(R^1)-COOC_2H_5$ --.

Col. 20, line 29, "similarly" should read -- Similarly --.

Col. 23, line 53, "1Bromo" should read -- 1-Bromo --.

Signed and Sealed this

Eighth Day of December 1981

[SEAL]

Attest:

*Attesting Officer*

GERALD J. MOSSINGHOFF

*Commissioner of Patents and Trademarks*